(12) United States Patent
Bigg et al.

(10) Patent No.: US 7,534,805 B2
(45) Date of Patent: May 19, 2009

(54) IMIDAZOLE DERIVATIVES, THEIR PREPARATION AND THEIR USE AS MEDICAMENTS

(75) Inventors: Dennis Bigg, Gif-sur-Yvette (FR); Anne-Marie Liberatore, Auffargis (FR); Dominique Pons, Paris (FR)

(73) Assignee: Societe de Conseils de Recherches Et d'Applications Scientifiques (S.C.R.A.S.), Paris (FR)

( * ) Notice: Subject to any disclaimer, the term of this patent is extended or adjusted under 35 U.S.C. 154(b) by 354 days.

(21) Appl. No.: 10/557,303

(22) PCT Filed: May 26, 2004

(86) PCT No.: PCT/FR2004/001297

§ 371 (c)(1),
(2), (4) Date: Nov. 16, 2005

(87) PCT Pub. No.: WO2004/106307

PCT Pub. Date: Dec. 9, 2004

(65) Prior Publication Data

US 2007/0066542 A1   Mar. 22, 2007

(30) Foreign Application Priority Data

May 27, 2003  (FR)  .................... 03 06403
Jun. 4, 2003   (FR)  .................... 03 06712

(51) Int. Cl.
*A61K 31/4174*  (2006.01)
*C07D 233/60*   (2006.01)

(52) U.S. Cl. .................... 514/396; 548/343.5

(58) Field of Classification Search .................. 514/396; 548/343.5
See application file for complete search history.

(56) References Cited

U.S. PATENT DOCUMENTS 6,444,687 B1 * 9/2002 Stamford et al. ............ 514/318

FOREIGN PATENT DOCUMENTS

WO   WO 99/02155   *   1/1999

OTHER PUBLICATIONS

Le Wang,K. W. Woods, Q. Li,K.J. Barr,et al: "Potent, orally, active heterocycle-based . . . evaluation"J. Med. Chem., vol. 45, 2002, pp. 1697-1711, XP002304485.

* cited by examiner

*Primary Examiner*—Kamal A. Saeed
*Assistant Examiner*—Janet L. Coppins
(74) *Attorney, Agent, or Firm*—Charles A. Muserlian

(57) ABSTRACT

Novel imidazole compounds of the formula

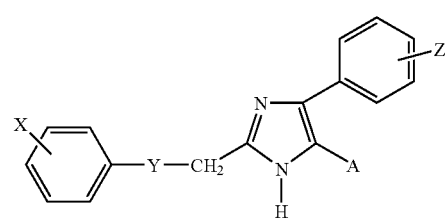

wherein the substituents are as defined in the application having antitumoral activity and use thereof.

21 Claims, No Drawings

IMIDAZOLE DERIVATIVES, THEIR PREPARATION AND THEIR USE AS MEDICAMENTS

This application is a 371 of PCT/FR2004/001297 filed May 26, 2004

A subject of the present application is novel imidazole derivatives. The invention also relates to pharmaceutical compositions containing these derivatives and their use for the preparation of a medicament.

Imidazole derivatives according to the present invention have an anti-tumorous activity and in particular a tubulin polymerization-inhibiting activity.

Target of several anticancer medicaments, tubulin is a small protein which, by polymerizing, produces microtubules of the achromatic spindle which allow cell division during mitosis. Vinca alkaloids inhibit its polymerization, whereas paclitaxel and docetaxel stabilize it excessively. In both cases, mitosis cannot take place normally, which hinders cell proliferation.

Because of their anti-tumorous activity, the compounds according to the invention can be used for the treatment of tumors or cancers including cancers of the oesophagus, stomach, intestines, rectum, oral cavity, pharynx, larynx, lung, colon, breast, cervix uteri, corpus endometrium, ovaries, prostate, testicles, bladder, kidneys, liver, pancreas, bone, connective tissues, skin, eyes, brain, melanomas and cancers of the central nervous system, as well as cancer of the thyroid, leukemia, Hodgkin's disease, lymphomas other than Hodgkin's, multiple myelomas and others. Moreover these compounds could also be used to treat certain viral infections such as acquired immunodeficiency syndrome, hepatitis C as well as autoimmune diseases and certain degenerative diseases.

A subject of the invention is therefore a compound of general formula (I)

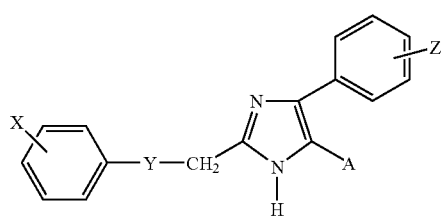

(I)

in racemic, enantiomeric form or any combinations of these forms and in which

X represents one or more identical or different substituents chosen from H and halo;

Y represents —O— or —S—;

A represents H or $(C_1-C_6)$alkyl;

Z represents one or more identical or different substituents chosen from:

$(C_1-C_6)$alkyl optionally substituted by one or more identical or different halo radicals;

aryl optionally substituted by one or more identical or different radicals chosen from: halo, nitro, cyano, hydroxy, $(C_1-C_6)$alkyl optionally substituted by one or more identical or different halo radicals, —$(CH_2)_n$—$NR_3R_4$, $(C_1-C_6)$alkyl-sulphonyl, $(C_1-C_6)$alkyl-thio, $(C_1-C_6)$alkoxy optionally substituted by one or more identical or different halo radicals, $(C_1-C_6)$alkoxy-carbonyl, phosphate, sulphate, glycoside and —NH—C(O)—CH($R_A$)—$NR_5R_6$;

aryl-$(C_1-C_6)$alkyl;

heteroaryl;

—$Z_1$—$Z'_1$;

—$NR_N$—C(O)—$Z'_2$; or

—$Z_2$—$Z'_2$;

$Z_1$ represents —O—, —C(O)—O—, —$NR_N$—C(O)— or —C(O)—$NR_N$—;

$Z'_1$ represents a $(C_1-C_{10})$alkyl radical; aryl-$(C_1-C_6)$alkyl, the aryl radical of which is optionally substituted by one or more identical or different halo radicals; or $(C_1-C_6)$alkyl substituted by one or more substituents chosen from halo, $(C_1-C_6)$alkoxy, $(C_1-C_6)$alkylthio and —$NR_1R_2$;

$R_1$ and $R_2$ represent, independently, H or $(C_1-C_6)$alkyl, or form together with the nitrogen atom to which they are attached, a heterocycloalkyl optionally substituted by $(C_1-C_6)$alkyl;

$Z_2$ represents —O—, —S—, —$SO_2$—, —C(O)—, —C(O)—$NR_N$— or —$NR_N$—;

$Z'_2$ represents an aryl or heteroaryl radical, the aryl and heteroaryl radicals being optionally substituted by one or more identical or different radicals chosen from:

halo, nitro, cyano, hydroxy, $(C_1-C_6)$alkyl optionally substituted by one or more identical or different halo radicals, $(C_1-C_6)$alkyl-thio, $(C_1-C_6)$alkyl-sulphonyl, $(C_1-C_6)$alkoxy optionally substituted by one or more identical or different halo radicals, aryl-alkoxy, $(C_1-C_6)$alkoxy-carbonyl, phosphate, sulphate, glycoside, —$(CH_2)_n$—$NR_3R_4$ and —NH—C(O)—CH($R_A$)—$NR_5R_6$;

$R_3$ and $R_4$ represent, independently, H, $(C_1-C_6)$alkyl, $(C_1-C_6)$alkyl-carbonyl or $(C_1-C_6)$alkyl-sulphonyl, or $R_3$ and $R_4$ form together with the nitrogen atom to which they are attached, a heteroaryl or a heterocycloalkyl optionally substituted by $(C_1-C_6)$alkyl;

$R_5$ and $R_6$ represent, independently, H or $(C_1-C_6)$alkyl;

$R_A$ represents the residue associated with the amino acid of formula $NH_2$—CH($R_A$)—C(O)—OH;

$R_N$ represents hydrogen or a $(C_1-C_6)$alkyl radical;

n represents an integer from 0 to 3; or a pharmaceutically acceptable salt thereof, to the exclusion of compounds in which A represents the hydrogen atom and Z the -3-$CF_3$ radical.

The invention clearly covers all the tautomeric forms of the compounds of formula (I) as defined above.

In the definitions indicated above, the expression halo (halogeno) represents the fluoro, chloro, bromo or iodo, preferably fluoro, chloro or bromo radical. The expression alkyl (unless otherwise specified), preferably represents a linear or branched alkyl radical having 1 to 6 carbon atoms, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2-trimethyl-propyl radicals. The term $(C_4-C_{10})$alkyl designates a linear or branched alkyl radical having 4 to 10 carbon atoms, such as radicals containing 4 to 6 carbon atoms as defined above but also heptyl, octyl, 1,1,2,2-tetramethyl-propyl, 1,1,3,3-tetramethyl-butyl, nonyl or decyl. The term $(C_1-C_{20})$alkyl designates an alkyl radical having 1 to 20 carbon atoms, linear or branched, such as the radicals containing 1 to 10 carbon atoms as defined above but also the radicals containing 11 to 20 carbon atoms such as undecyl, dodecyl, tridecyl, tetradecyl, pentadecyl, hexadecyl, heptadecyl, octadecyl, nonadecyl or eicosanyl.

The expression alkyl-sulphonyl preferably represents a radical in which the alkyl radical is as defined above such as for example, methylsulphonyl, ethylsulphonyl. Similarly the expression alkyl-carbonyl preferably represents a radical in which the alkyl radical is as defined above such as for example methylcarbonyl, ethylcarbonyl. The term ($C_1$-$C_6$) alkylthio designates radicals in which the alkyl radical is as defined above such as for example the methylthio, ethylthio radicals.

The term ($C_1$-$C_6$)alkoxy designates the radicals in which the alkyl radical is as defined above such as for example the methoxy, ethoxy, propyloxy or isopropyloxy radicals but also linear, secondary or tertiary butoxy, pentyloxy radicals. The term alkoxy-carbonyl preferably designates the radicals in which the alkoxy radical is as defined above such as for example methoxycarbonyl, ethoxycarbonyl.

The expression aryl represents an aromatic radical, constituted by a condensed ring or rings, such as for example the phenyl, naphthyl or fluorenyl radical. The expression heteroaryl designates an aromatic radical, constituted by a condensed ring or rings, with at least one ring containing one or more identical or different heteroatoms chosen from sulphur, nitrogen or oxygen. As an example of a heteroaryl radical, the pyrrolyl, imidazolyl, pyrazolyl, isothiazolyl, thiazolyl, isoxazolyl, oxazolyl, triazolyl, thiadiazolyl, pyridyl, pyrazinyl, pyrimidyl, quinolyl, isoquinolyl, quinoxalinyl, indolyl, benzoxadiazoyl, carbazolyl, purinyl, triazinyl, pyrrazolo-pyrimidyl but also thienyl, benzothienyl, furyl, benzofuryl or pyranyl radicals can be mentioned. The term aralkyl (arylalkyl) preferably designates the radicals in which the aryl and alkyl radicals are as defined above such as for example benzyl or phenethyl. The term arylalkoxy preferably designates the radicals in which the aryl and alkoxy radicals are as defined above such as for example benzyloxy or phenylethoxy.

The expression heterocycloalkyl designates a condensed monocyclic or bicyclic saturated system containing 2 to 7 carbon atoms and at least one heteroatom. This radical can contain several identical or different heteroatoms. Preferably, the heteroatoms are chosen from oxygen, sulphur or nitrogen. As examples of heterocycloalkyls containing at least one nitrogen atom, the pyrrolidine, imidazolidine, pyrrazolidine, isothiazolidine, thiazolidine, isoxazolidine, oxazolidine, piperidine, piperazine, azepane (azacycloheptane), azacyclooctane, diazepane, morpholine, decahydroisoquinoline (or decahydroquinoline) rings can be mentioned.

The expression phosphate represents the radical of formula —OP(O)(OR$_p$')(OR$_p$") in which R$_p$' and R$_p$" designate, independently, a radical chosen from: H, linear and branched ($C_1$-$C_{20}$)alkyl, aryl and arylalkyl.

The expression sulphate represents the radical of formula —OS(O)$_2$(OR) in which R designates a radical chosen from: H, linear or branched ($C_1$-$C_{20}$)alkyl, aryl and arylalkyl.

The expression glycoside represents radicals such as the glucosyl, maltosyl, glucuronyl radicals.

In the present application, R$_A$ represents the residue associated with the amino acid of formula NH$_2$—CH(R$_A$)—C(O)—OH. Preferably, R$_A$ represents the R$_{AA}$ radical associated with the natural amino acids of formula NH$_2$—CH(R$_{AA}$)—C(O)—OH which are glycine, alanine, valine, isoleucine, leucine, methionine, phenylalanine, tyrosine, tryptophan, serine, threonine, asparagine, glutamine, aspartic acid, glutamic acid, histidine, lysine, arginine, cysteine and proline.

Also, in the present application, the (CH$_2$)$_n$ radical represents a linear or branched hydrocarbon chain with n carbon atoms.

Also, according to the present application, when a radical has the formula —B—D—E with D representing for example —C(O)—NH—, this signifies that the carbon atom of —C(O)—NH— is linked to B and the nitrogen atom to E.

By pharmaceutically acceptable salt is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, benzenesulphonate, p-toluenesulphonate, pamoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

Preferably, the invention relates to a compound of formula (I) as defined above and characterized in that
X represents one or more identical or different substituents chosen from H and halo;
Y represents —O— or —S—;
A represents H or ($C_1$-$C_6$)alkyl;
Z represents one or more identical or different substituents chosen from:
($C_1$-$C_6$)alkyl optionally substituted by one or more identical or different halo radicals;
aryl optionally substituted by one or more identical or different radicals chosen from: halo, nitro, cyano, hydroxy, ($C_1$-$C_6$)alkyl optionally substituted by one or more identical or different halo radicals, and ($C_1$-$C_6$)alkoxy optionally substituted by one or more identical or different halo radicals;
heteroaryl;
—Z$_1$—Z'$_1$;
—NH—C(O)—Z'$_2$; or
—Z$_2$—Z'$_2$;
Z$_1$ represents —O—, —NH—C(O)— or —C(O)—NH—;
Z'$_1$ represents a ($C_4$-$C_{10}$)alkyl radical; aryl-($C_1$-$C_6$)alkyl the aryl radical of which is optionally substituted by one or more identical or different halo radicals; or ($C_1$-$C_6$) alkyl substituted by one or more substituients chosen from: halo, ($C_1$-$C_6$)alkoxy, ($C_1$-$C_6$)alkylthio and —NR$_1$R$_2$;
R$_1$ and R$_2$ represent, independently, H or ($C_1$-$C_6$)alkyl, or form together with the nitrogen atom to which they are attached, a heterocycloalkyl optionally substituted by ($C_1$-$C_6$)alkyl;
Z$_2$ represents —O—, —S—, —SO$_2$—, —C(O)— or —C(O)—NH—;
Z'$_2$ represents an aryl radical optionally substituted by one or more identical or different radicals chosen from: halo, nitro, cyano, hydroxy, ($C_1$-$C_6$)alkyl optionally substituted by one or more identical or different halo radicals, and ($C_1$-$C_6$)alkoxy optionally substituted by one or more identical or different halo radicals; or a pharmaceutically acceptable salt thereof.

Preferably, the invention relates to a compound of formula (I) as defined above and characterized in that A represents H and Y represents —O—; or a pharmaceutically acceptable salt thereof.

Preferably, the invention relates to a compound of formula (I) as defined above and characterized in that X represents H; or a pharmaceutically acceptable salt thereof.

Preferably, the invention relates to a compound of formula (I) as defined above and characterized in that
Z represents one or more substituents, identical or different, in meta and/or para position and chosen from heteroaryl and —Z$_2$—Z'$_2$;

$Z_2$ represents —O—, —S—, —$SO_2$—, —C(O)— or —C(O)—NH—;

$Z'_2$ represents one of the phenyl or naphthyl radicals optionally substituted by one or more identical or different radicals chosen from halo, nitro, cyano, hydroxy, ($C_1$-$C_6$)alkyl optionally substituted by one or more identical or different halo radicals, and ($C_1$-$C_6$)alkoxy optionally substituted by one or more identical or different halo radicals; or a pharmaceutically acceptable salt thereof.

Preferably also, the invention relates to a compound of formula (I) as defined above and characterized in that Z represents a heteroaryl;

—$Z_1$—$Z'_1$ in which either $Z_1$ represents —O—, —$NR_N$—C(O)— or —C(O)—$NR_N$— and $Z'_1$ represents the benzyl radical;

or $Z_1$ represents —O—, —C(O)—O—, —$NR_N$—C(O)— or —C(O)—$NR_N$— and $Z'_1$ represents a ($C_1$-$C_6$)alkyl radical substituted by one or more substituents chosen from: halo, ($C_1$-$C_6$)alkoxy, ($C_1$-$C_6$)alkylthio and —$NR_1R_2$;

$R_1$ and $R_2$ represent, independently, H or ($C_1$-$C_6$)alkyl, or form together with the nitrogen atom to which they are attached, a heterocycloalkyl;

—$Z_2$—$Z'_2$ in which $Z_2$ represents —O—, —S—, —$SO_2$—, —C(O)—, —C(O)—$NR_N$— or —$NR_N$—;

$Z'_2$ represents a phenyl radical or phenyl substituted by one or more identical or different radicals chosen from:

halo, nitro, cyano, hydroxy, ($C_1$-$C_6$)alkyl optionally substituted by one or more identical or different halo radicals, ($C_1$-$C_6$)alkyl-thio, ($C_1$-$C_6$)alkyl-sulphonyl, ($C_1$-$C_6$)alkoxy optionally substituted by one or more identical or different halo radicals, aryl-alkoxy, ($C_1$-$C_6$)alkoxy-carbonyl, —($CH_2$)$_n$—$NR_3R_4$ and —NH—C(O)—CH($R_A$)—$NR_5R_6$;

$R_3$ and $R_4$ represent, independently, H, ($C_1$-$C_6$)alkyl or ($C_1$-$C_6$)alkyl-carbonyl;

$R_5$ and $R_6$ represent, independently, H or ($C_1$-$C_6$)alkyl;

$R_A$ represents the residue associated with the amino acid of formula $NH_2$—CH($R_A$)—C(O)—OH;

$R_N$ represents hydrogen or a ($C_1$-$C_6$)alkyl radical; or a pharmaceutically acceptable salt thereof.

Preferably also, the invention relates to a compound of formula (I) as defined above and characterized in that Z represents one or more substituents, identical or different, of formula —$Z_2$—$Z'_2$, and very preferentially Z is in meta and/or para position; or a pharmaceutically acceptable salt thereof.

The invention very preferentially relates to a compound of formula (I) as defined above and characterized in that $Z_2$ represents —O—, —S—, —$SO_2$— or —C(O)—, and more particularly —O—; or a pharmaceutically acceptable salt thereof.

The invention very preferentially relates to a compound of formula (I) as defined above and characterized in that $Z_2$ also preferentially represents —$NR_N$—; or a pharmaceutically acceptable salt thereof.

Preferentially, $Z'_2$ represents phenyl or phenyl substituted by one or more identical or different radicals chosen from:

halo, nitro, cyano, hydroxy, ($C_1$-$C_6$)alkyl optionally substituted by one or more identical or different halo radicals, ($C_1$-$C_6$)alkyl-thio, ($C_1$-$C_6$)alkyl-sulphonyl, ($C_1$-$C_6$)alkoxy optionally substituted by one or more identical or different halo radicals, benzyloxy, ($C_1$-$C_6$)alkoxy-carbonyl, phosphate, —($CH_2$)$_n$—$NR_3R_4$ and —NH—C(O)—CH($R_A$)—$NR_5R_6$;

$R_3$ and $R_4$ represent, independently, H, ($C_1$-$C_6$)alkyl, ($C_1$-$C_6$)alkyl-carbonyl or ($C_1$-$C_6$)alkyl-sulphonyl;

$R_N$ represents hydrogen or a ($C_1$-$C_6$)alkyl radical;

$R_5$ and $R_6$ represent, independently, H or ($C_1$-$C_6$)alkyl; and $R_A$ represents the residue associated with the amino acid of formula $NH_2$—CH($R_A$)—C(O)—OH, and more particularly $Z'_2$ represents phenyl substituted by one or more identical or different radicals chosen from: halo, nitro, cyano, hydroxy, ($C_1$-$C_6$)alkyl-sulphonyl, ($C_1$-$C_6$)alkoxy, —($CH_2$)$_n$—$NR_3R_4$ and —NH—C(O)—CH($R_A$)—$NR_5R_6$;

$R_3$ and $R_4$ represent, independently, H, ($C_1$-$C_6$)alkyl or ($C_1$-$C_6$)alkyl-carbonyl;

$R_5$ and $R_6$ represent, independently, H or ($C_1$-$C_6$)alkyl; or a pharmaceutically acceptable salt thereof.

The invention also very preferentially relates to a compound of formula (I) as defined above and characterized in that $Z'_2$ represents phenyl substituted by at least two identical or different radicals chosen from: fluoro, nitro, cyano, hydroxy, ($C_1$-$C_6$)alkyl-sulphonyl, ($C_1$-$C_6$)alkoxy, —$NH_2$ and —NH—C(O)—CH($R_A$)—$NR_5R_6$; $R_5$ and $R_6$ represent, independently, H or ($C_1$-$C_6$)alkyl; or a pharmaceutically acceptable salt thereof.

Preferentially also, the invention relates to a compound of formula (I) as defined above and characterized in that $Z'_2$ represents the pyridinyl, pyrimidinyl, pyrazinyl, triazolyl, furyl, thienyl, purinyl, triazinyl, pyrrazolo-pyrimidinyl, quinoxalinyl or indolyl radical, each of these radicals being optionally substituted by one or more identical or different radicals chosen from: halo, nitro, cyano, hydroxy, ($C_1$-$C_6$)alkyl and —$NH_2$; or a pharmaceutically acceptable salt thereof.

A subject of the invention is also compounds as illustrated in the experimental part and characterized in that they correspond to one of the following formulae:

4-[4-(4-fluorophenoxy)phenyl]-2-(phenoxymethyl)-1H-imidazole;

4-(1,1'-biphenyl-4-yl)-2-[(phenylthio)methyl]-1H-imidazole;

4-(1,1'-biphenyl-4-yl)-2-(phenoxymethyl)-1H-imidazole;

4-[4-(4-fluorophenoxy)phenyl]-2-[(phenylthio)methyl]-1H-imidazole;

2-[(4-fluorophenoxy)methyl]-4-[4-(4-fluorophenoxy)phenyl]-1H-imidazole;

2-(phenoxymethyl)-4-[4-(phenylthio)phenyl]-1H-imidazole;

2-(phenoxymethyl)-4-[4-(phenylsulphonyl)phenyl]-1H-imidazole;

4-{4-[(2-fluorobenzyl)oxy]phenyl}-2-(phenoxymethyl)-1H-imidazole;

2-(phenoxymethyl)-4-(4-phenoxyphenyl)-1H-imidazole trifluoroacetate;

4-[4-(4-bromophenoxy)phenyl]-2-(phenoxymethyl)-1H-imidazole trifluoroacetate;

4-[4-(1H-imidazol-1-yl)phenyl]-2-(phenoxymethyl)-1H-imidazole;

4-[4-(4-methoxyphenoxy)phenyl]-2-(phenoxymethyl)-1H-imidazole;

4-(4-hexylphenyl)-2-(phenoxymethyl)-1H-imidazole;

4-(4-butoxyphenyl)-2-(phenoxymethyl)-1H-imidazole;

4-[4-(4-nitrophenoxy)phenyl]-2-(phenoxymethyl)-1H-imidazole;

4-(2-{4-[2-(phenoxymethyl)-1H-imidazol-4-yl]phenoxy}ethyl)morpholine;
1-(2-{4-[2-(phenoxymethyl)-1H-imidazol-4-yl]phenoxy}ethyl)piperidine hydrochloride;
N,N-dimethyl-N-(2-{4-[2-(phenoxymethyl)-1H-imidazol-4-yl]phenoxy}ethyl)amine hydrochloride;
4-[4-(2-methoxyethoxy)phenyl]-2-(phenoxymethyl)-1H-imidazole;
2-(phenoxymethyl)-4-[4-(4,4,4-trifluorobutoxy)phenyl]-1H-imidazole;
4-[4-(4-fluorophenoxy)phenyl]-5-methyl-2-(phenoxymethyl)-1H-imidazole;
4-fluoro-N-{4-[2-(phenoxymethyl)-1H-imidazol-4-yl]phenyl}benzamide;
4-{4-[2-(phenoxymethyl)-1H-imidazol-4-yl]phenoxy}benzonitrile;
ethyl 4-[2-(phenoxymethyl)-1H-imidazol-4-yl]benzoate;
ethyl 4-{4-[2-(phenoxymethyl)-1H-imidazol-4-yl]phenoxy}benzoate;
4-{4-[4-(methylthio)phenoxy]phenyl}-2-(phenoxymethyl)-1H-imidazole;
4-{4-[4-(methylsulphonyl)phenoxy]phenyl}-2-(phenoxymethyl)-1H-imidazole;
4-{4-[2-(phenoxymethyl)-1H-imidazol-4-yl]phenoxy}aniline hydrochloride;
{4-[2-(phenoxymethyl)-1H-imidazol-4-yl]phenyl}phenyl methanone trifluoroacetate;
N-(4-fluorophenyl)-4-[2-(phenoxymethyl)-1H-imidazol-4-yl]benzamide trifluoroacetate;
4-[4-(3-nitrophenoxy)phenyl]-2-(phenoxymethyl)-1H-imidazole;
3-{4-[2-(phenoxymethyl)-1H-imidazol-4-yl]phenoxy}aniline hydrochloride;
4-{4-[4-(benzyloxy)phenoxy]phenyl}-2-(phenoxymethyl)-1H-imidazole;
4-{4-[2-(phenoxymethyl)-1H-imidazol-4-yl]phenoxy}phenol;
4-[4-(3-fluorophenoxy)phenyl]-2-(phenoxymethyl)-1H-imidazole;
N-(4-{4-[2-(phenoxymethyl)-1H-imidazol-4-yl]phenoxy}phenyl)acetamide;
2-nitro-4-{4-[2-(phenoxymethyl)-1H-imidazol-4-yl]phenoxy}aniline trifluoroacetate;
N-methyl-N-(4-{4-[2-(phenoxymethyl)-1H-imidazol-4-yl]phenoxy}phenyl)amine;
3-{4-[2-(phenoxymethyl)-1H-imidazol-4-yl]phenoxy}benzonitrile;
4-[4-(2-nitrophenoxy)phenyl]-2-(phenoxymethyl)-1H-imidazole;
2-{4-[2-(phenoxymethyl)-1H-imidazol-4-yl]phenoxy}aniline hydrochloride;
1-(4-{4-[2-(phenoxymethyl)-1H-imidazol-4-yl]phenoxy}phenyl)methanamine hydrochloride;
1-(3-{4-[2-(phenoxymethyl)-1H-imidazol-4-yl]phenoxy}phenyl)methanamine hydrochloride;
4-[4-(3-bromophenoxy)phenyl]-2-(phenoxymethyl)-1H-imidazole;
2-fluoro-4-{4-[2-(phenoxymethyl)-1H-imidazol-4-yl]phenoxy}aniline hydrochloride;
4-[4-(3-chlorophenoxy)phenyl]-2-(phenoxymethyl)-1H-imidazole;
4-[4-(3,5-difluorophenoxy)phenyl]-2-(phenoxymethyl)-1H-imidazole;
4-(4-benzylphenyl)-2-(phenoxymethyl)-1H-imidazole;
4-[4-(3-methylphenoxy)phenyl]-2-(phenoxymethyl)-1H-imidazole;
4-[4-(2-chlorophenoxy)phenyl]-2-(phenoxymethyl)-1H-imidazole hydrochloride;
4-[4-(2-fluorophenoxy)phenyl]-2-(phenoxymethyl)-1H-imidazole;
4-[4-(3,4-difluorophenoxy)phenyl]-2-(phenoxymethyl)-1H-imidazole;
N$^1$-(4-{4-[2-(phenoxymethyl)-1H-imidazol-4-yl]phenoxy}phenyl)glycinamide hydrochloride;
4-[4-(2,5-difluorophenoxy)phenyl]-2-(phenoxymethyl)-1H-imidazole;
4-[4-(2,4-difluorophenoxy)phenyl]-2-(phenoxymethyl)-1H-imidazole;
4-[4-(2,3-difluorophenoxy)phenyl]-2-(phenoxymethyl)-1H-imidazole;
4-[4-(2,6-difluorophenoxy)phenyl]-2-(phenoxymethyl)-1H-imidazole.

A subject of the invention is also a process for the preparation of compounds according to the invention characterized in that a compound of formula

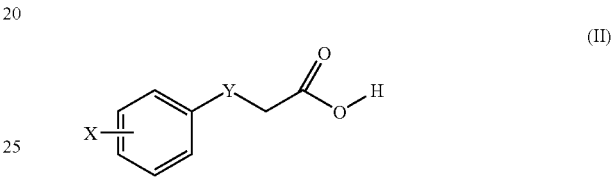

(II)

in which X and Y have the meaning indicated above, is reacted with a base in order to form compound (II) in salified form, then with the α-halogeno-ketone of formula

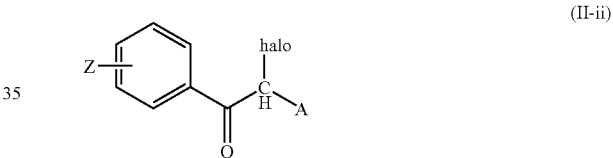

(II-ii)

in which Z and A have the meaning indicated above, in an inert solvent,
then the keto-ester thus obtained is cyclized in the presence of an ammonium salt in order to produce the compound of formula (I).

The acid of general formula (II) is treated with a base such as $Cs_2CO_3$ in a solvent such as methanol or ethanol. The α-halogeno-ketone of general formula (II-ii) is added in an inert solvent such as dimethylformamide to the recovered cesium salt. The intermediate ketoester leads, by heating under reflux in an aprotic apolar solvent such as xylene (mixture of isomers) or toluene, in the presence of a large excess of ammonium salt such as ammonium acetate (15 or 20 equivalents for example) to the imidazole derivative of general formula (I) (the water formed being eliminated during the reaction).

The α-halogeno-ketone of general formula (II-ii) can be prepared from the following ketone derivative:

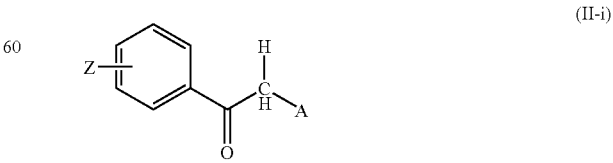

(II-i)

in which Z and A are as defined above.

The ketone derivative of general formula (II-ii) is converted to the corresponding α-halogeno-ketone of general formula (II-ii). Preferably, the ketone derivative of general formula (II-i) is converted to α-bromo-ketone, by reaction with a bromination agent such as CuBr₂ (*J. Org. Chem.* (1964), 29, 3459), bromine in ethanol or acetic acid (*J. Het. Chem.* (1988), 25, 337; *J. Med Chem.* (1988), 31(10), 1910-1918), N-bromosuccinimide (*J. Amer. Chem. Soc.* (1980), 102, 2838) in the presence of acetic acid in a solvent such as ethyl acetate or dichloromethane, HBr in ether (*Biorg. Med. Chem. Lett.* (1996), 6(3), 253-258; *J. Am. Chem. Soc.* (1999), 121, 24) or also using a bromination resin (*J. Macromol. Sci. Chem.* (1977), A11, (3) 507-514).

The compounds (II-i) can be prepared according to the procedures known to a person skilled in the art (Schmid, C. R.; Sluka, J. P.; Duke, K. M. *Tetrahedron Lett.* 1999, 40, 675-678; Hogenkamp, D. J.; Upasani, R.; Nguyen, P.; WO 00/57877. *Chem. Abstr.* 2000, 133, 28179).

The compounds of general formula (I) can also be prepared by condensing under reflux in a polar inert solvent such as dimethylformamide, a starting compound of formula (II-iii) in which X and Y have the meaning indicated above and the α-halogeno-ketone of general formula (II-ii) in which Z and A are as defined above.

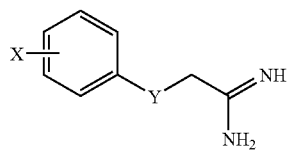
(II-iii)

A subject of the invention is therefore also a process for preparation of a compound according to the invention and characterized in that a compound of formula (II-iii)

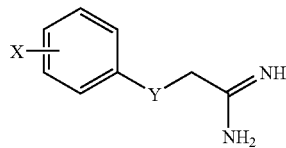

in which X and Y have the meaning indicated above, and the α-halogeno-ketone of general formula (II-ii) in which Z and A are as defined above is condensed under reflux in a polar inert solvent.

The compounds of formula (I) of the present invention have useful pharmacological properties. It was thus that it was discovered that the compounds of formula (I) of the present invention possess an anti-tumorous activity and more particularly a tubulin polymerization-inhibiting activity.

The compounds of the present invention can thus be used in different therapeutic applications. They can advantageously be used for the treatment of tumors or cancers as defined previously and preferably cancers of the colon, prostate, pancreas and melanomas. Hereafter, in the experimental part, an illustration will be found of the pharmacological properties of the compounds of the invention.

A subject of the present application is also pharmaceutical compositions containing, as active ingredient, at least one compound of formula (I) as defined above, as well as the addition salts with pharmaceutically acceptable mineral or organic acids of said compound of formula I, in combination with a pharmaceutically acceptable support.

A subject of the present application is also the use of a compound of formula (I) according to the present invention, for the preparation of an anti-tumorous medicament.

A subject of the present application is also the use of a compound of formula (I) according to the present invention, for the preparation of a medicament intended to inhibit tubulin polymerization.

Imidazole derivatives have been described in the application WO 01/44201 as antagonists of the Y5 receptors.

A subject of the present application is therefore also the use of a compound of formula (I')

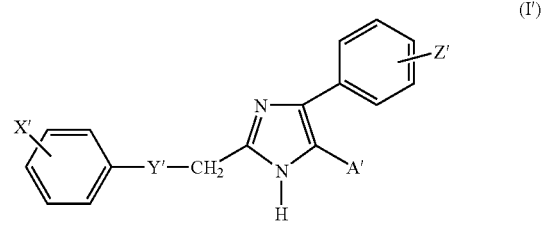

in racemic, enantiomeric form or any combinations of these forms, and in which

X' represents one or more identical or different substituents chosen from H and halo;

Y' represents —O— or —S—;

A' represents H or (C₁-C₆)alkyl;

Z' represents one or more identical or different substituents chosen from:

(C₁-C₆)alkyl optionally substituted by one or more identical or different halo radicals;

aryl optionally substituted by one or more identical or different radicals chosen from: halo, nitro, cyano, hydroxy, (C₁-C₆)alkyl optionally substituted by one or more identical or different halo radicals, —(CH₂)ₙ—NR₃R₄, (C₁-C₆)alkyl-sulphonyl, (C₁-C₆)alkyl-thio, (C₁-C₆)alkoxy optionally substituted by one or more identical or different halo radicals, (C₁-C₆)alkoxy-carbonyl, phosphate, sulphate, glycoside and —NH—C(O)—CH(R₄)—NR₅R₆;

aryl-(C₁-C₆)alkyl;

heteroaryl;

—Z₁—Z'₁;

—NRₙ—C(O)—Z'₂; or

—Z₂—Z'₂;

Z₁ represents —O—, —C(O)—O—, —NRₙ—C(O)— or —C(O)—NRₙ—;

Z'₁ represents a (C₁-C₁₀)alkyl radical; aryl-(C₁-C₆)alkyl the aryl radical of which is optionally substituted by one or more identical or different halo radicals; or (C₁-C₆)alkyl substituted by one or more substituents chosen from: halo, (C₁-C₆)alkoxy, (C₁-C₆)alkylthio and —NR₁R₂;

R₁ and R₂ represent, independently, H or (C₁-C₆)alkyl, or form together with the nitrogen atom to which they are attached, a heterocycloalkyl optionally substituted by (C₁-C₆)alkyl;

Z₂ represents —O—, —S—, —SO₂—, —C(O)—, —C(O)—NRₙ— or —NRₙ—;

Z'₂ represents an aryl or heteroaryl radical, the aryl and heteroaryl radicals being optionally substituted by one or more identical or different radicals chosen from:

halo, nitro, cyano, hydroxy, $(C_1$-$C_6)$alkyl optionally substituted by one or more identical or different halo radicals, $(C_1$-$C_6)$alkyl-thio, $(C_1$-$C_6)$alkyl-sulphonyl, $(C_1$-$C_6)$alkoxy optionally substituted by one or more identical or different halo radicals, aryl-alkoxy, $(C_1$-$C_6)$ alkoxy-carbonyl, phosphate, sulphate, glycoside, —$(CH_2)_n$—$NR_3R_4$ and —NH—C(O)—CH($R_A$)—$NR_5R_6$;

$R_3$ and $R_4$ represent, independently, H, $(C_1$-$C_6)$alkyl, $(C_1$-$C_6)$alkyl-carbonyl or $(C_1$-$C_6)$alkyl-sulphonyl, or $R_3$ and $R_4$ form together with the nitrogen atom to which they are attached, a heteroaryl or a heterocycloalkyl optionally substituted by $(C_1$-$C_6)$alkyl;

$R_5$ and $R_6$ represent, independently, H or $(C_1$-$C_6)$alkyl;

$R_A$ represents the residue associated with the amino acid of formula $NH_2$—CH($R_A$)—C(O)—OH;

$R_N$ represents hydrogen or a $(C_1$-$C_6)$alkyl radical;

n represents an integer from 0 to 3; or a pharmaceutically acceptable salt of these compounds, for the preparation of an anti-tumorous medicament.

A subject of the present application is also the use of the compounds of formula (I') as defined above, for the preparation of a medicament intended to inhibit tubulin polymerization.

The compounds of the present invention can be administered alone or in combination with other agents with anti-tumorous activity. Among the agents with anti-tumorous activity, there can be mentioned: topoisomerase I inhibitors such as diflomotecan, irinotecan or topotecan; topoisomerase II inhibitors; alkylating agents such as cyclophosphamide, phosphamides or melphalan; platinum derivatives such as cisplatin, carboplatin or oxaliplatin; antibiotic agents such as bleomycin or mitomycin; antimetabolites such as 5-fluorouracil; and hormonal agents.

Administration of a composition according to the invention can also be combined with radiotherapy.

The pharmaceutical composition can be in the form of a solid, for example, powders, granules, tablets, gelatin capsules. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in the form of a liquid, for example, solutions, emulsions, suspensions or syrups. Appropriate liquid supports can be, for example, water, organic solvents such as glycerol or the glycols, as well as their mixtures, in varying proportions, in water, to which oils or pharmaceutically acceptable fats have been added. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference.

The examples are presented in order to illustrate the above procedures and should in no event be considered as a limit to the scope of the invention.

EXPERIMENTAL PART

EXAMPLE 1

4-[4-(4-fluorophenoxy)phenyl]-2-(phenoxymethyl)-1H-imidazole 1.1) 1-[4-(4-fluorophenoxy)phenyl]ethanone 17.7 ml of 4-fluoroacetophone (0.145 mol), 17.84 g of 4-fluorophenol (0.16 mol) and potassium carbonate (50 g, 0.36 mol) in 220 ml of anhydrous dimethylformamide are heated under reflux for 4 hours.

The mixture is cooled down then 200 ml of ethyl acetate and 200 ml of water are added. After decantation, the organic phase is recovered, washed with a 2N soda solution then with a saturated solution of sodium chloride. The organic phase is then dried over $Na_2SO_4$ and the solvent is evaporated off. The residue is then retreated for 30 minutes under stirring in 50 ml of isopentane then filtered on frit. A beige-coloured powder is obtained.

NMR $^1$H (δ ppm, DMSO): 2.53 (s, 3H); 7.01-7.03 (d, 2H); 7.16-7.31 (m, 4H); 7.96-7.99 (d, 2H)

Melting point: 70° C.

1.2) 2-bromo-1-[4-(4-fluorophenoxy)phenyl]ethanone

A solution of 1-[4-(4-fluorophenoxy)phenyl]ethanone (17.7 g, 0.077 mol) in 220 ml of ethanol is cooled down to approximately 0° C. Bromine (4.8 ml, 0.096 mol) is added dropwise with a syringe. The temperature is allowed to return to ambient temperature, followed by stirring for 2 hours. After evaporation of the solvent then stirring for 10 hours in isopentane, the residue is filtered on frit and dried under a vacuum chamber bell jar. A beige-coloured powder is obtained.

NMR $^1$H (δ ppm, DMSO): 4.85 (s, 2H); 7.03-7.05 (d, 2H); 7.18-7.32 (m, 4H); 8.00-8.02 (d, 2H)

Melting point: 56° C.

1.3) 4-[4-(4-fluorophenoxy)phenyl]-2-(phenoxymethyl)-1H-imidazole

A mixture containing phenoxyacetic acid (0.5 g, 3.3 mmol) and cesium carbonate (0.53 g, 1.65 mmol) in 10 ml of anhydrous methanol is stirred for one hour. This mixture is evaporated to dryness then diluted with 20 ml of dimethylformamide. 1 g of 2-bromo-1-[4-(4-fluorophenoxy)phenyl] ethanone (3.3 mmol) prepared previously is added then the resulting mixture is stirred for 2 hours. The solvent is evaporated off using a diaphragm pump. 30 ml of ethyl acetate are added and the cesium bromide is filtered on frit. After evaporation of the solvent, the residue is diluted with 50 ml of xylene then ammonium acetate (3.8 g, 0.066 mol) is added and the mixture, maintained by a Dean Stark apparatus, is heated under reflux for 2 hours, followed by pouring into iced water to which 50 ml of ethyl acetate is added. After decantation, the organic phase is washed with a saturated solution of sodium chloride. The organic phase is then dried over magnesium sulphate and the solvent is evaporated off. The oil obtained crystallizes from isopropyl ether and a few drops of ethanol, followed by stirring then filtering on frit while rinsing with isopropyl ether and isopentane before drying under vacuum. The solid obtained is purified by chromatography on a silica column (eluent: ethyl acetate-heptane: 1-3). After evaporation of the solvent, the solid is washed in isopropyl ether then filtered on frit. A beige-coloured powder is obtained.

NMR $^1$H (δ ppm, DMSO): 5.08 (s, 2H); 6.94-7.79 (m, 14H); 12.38-12.72 (broad s, 1H MH+ experimental=361.1; MH+ theoretical=360.39

% C, 73.32; % H, 4.75; % N, 7.77 (theoretical); % C, 73.17; % H, 4.78; % N, 7.63; (measured).

Melting point: 188-190° C.

EXAMPLE 2

4-(1,1'-biphenyl-4-yl)-2-[(phenylthio)methyl]-1H-imidazole

This compound is synthesized according to a method analogous to that described in Example 1.

MH+ experimental=343.10; MH+ theoretical=342.46

Melting point: 150-152° C.

EXAMPLE 3

4-(1,1'-biphenyl-4-yl)-2-(phenoxymethyl)-1H-imidazole

This compound is synthesized according to a method analogous to that described in Example 1.

MH+ experimental=327.20; MH+ theoretical=326.40

Melting point: 185-187° C.

EXAMPLE 4

4-[4-(4-fluorophenoxy)phenyl]-2-[(phenylthio)methyl]-1H-imidazole

This compound is synthesized according to a method analogous to that described in Example 1.

MH+ experimental=377.10; MH+ theoretical=376.45

Melting point: 108-110° C.

EXAMPLE 5

2-[(4-fluorophenoxy)methyl]-4-[4-(4-fluorophenoxy)phenyl]-1H-imidazole

This compound is synthesized according to a method analogous to that described in Example 1.

MH+ experimental=379.00; MH+ theoretical=378.38

Melting point: 193-195° C.

EXAMPLE 6

2-(phenoxymethyl)-4-[4-(phenylthio)phenyl]-1H-imidazole

This compound is synthesized according to a method analogous to that described in Example 1.

MH+ experimental=359.10; MH+ theoretical=358.46

Melting point: 144-146° C.

EXAMPLE 7

2-(phenoxymethyl)-4-[4-(phenylsulphonyl)phenyl]-1H-imidazole

A solution of hydrogen peroxide (1.3 ml of a 30% solution in water) is added to 0.133 g (0.00037 mol) of 2-(phenoxymethyl)-4-[4-(phenylthio)phenyl]-1H-imidazole dissolved in 1 ml of acetic acid followed by stirring for approximately 20 hours then evaporation to dryness. 20 ml of water and 30 ml of ethyl acetate are then added. The organic phase is extracted then dried over sodium sulphate. After evaporation of the solvent, the residue obtained is treated with a mixture of solvents such as isopentane-diethyl ether in a proportion of 1-1. After filtration on frit, the solid obtained is washed with diethyl ether then dried in order to obtain a pale yellow-coloured powder.

NMR $^1$H (δ ppm, DMSO): 5.09 (s, 2H); 6.95-8.02 (m, 15H); 12.38-12.72 (broad s, 1H)

MH+ experimental=391.20; MH+ theoretical=390.46

Melting point: 192-194° C.

EXAMPLE 8

4-{4-[(2-fluorobenzyl)oxy]phenyl}-2-(phenoxymethyl)-1H-imidazole

This compound is synthesized according to a method analogous to that described in Example 1.

MH+ experimental=375.00; MH+ theoretical=374.41

Melting point: 182-183° C.

EXAMPLE 9

2-(phenoxymethyl)-4-(4-phenoxyphenyl)-1H-imidazole trifluoroacetate

This compound is synthesized according to a method analogous to that described in Example 1.

MH+ experimental=343.20; MH+ theoretical=342.40

Melting point: 112-114° C.

EXAMPLE 10

4-[4-(4-bromophenoxy)phenyl]-2-(phenoxymethyl)-1H-imidazole trifluoroacetate

This compound is synthesized according to a method analogous to that described in Example 1.

MH+ experimental=421.10; MH+ theoretical=421.29

Melting point: 174-176° C.

EXAMPLE 11

4-[4-(1H-imidazol-1-yl)phenyl]-2-(phenoxymethyl)-1H-imidazole This compound is synthesized according to a method analogous to that described in Example 1.

MH+ experimental=317.20; MH+ theoretical=316.36

Melting point: 194-196° C.

EXAMPLE 12

4-[4-(4-methoxyphenoxy)phenyl]-2-(phenoxymethyl)-1H-imidazole

This compound is synthesized according to a method analogous to that described in Example 1.

MH+ experimental=373.20; MH+ theoretical=373.42

Melting point: 132-134° C.

EXAMPLE 13

4-(4-hexylphenyl)-2-(phenoxymethyl)-1H-imidazole

This compound is synthesized according to a method analogous to that described in Example 1.
MH+ experimental=335.20; MH+ theoretical=334.46
Melting point: 151-153° C.

EXAMPLE 14

4-(4-butoxyphenyl)-2-(phenoxymethyl)-1H-imidazole

This compound is synthesized according to a method analogous to that described in Example 1.
MH+ experimental=323.20; MH+ theoretical=322.41
Melting point: 179-181° C.

EXAMPLE 15

4-[4-(4-nitrophenoxy)phenyl]-2-(phenoxymethyl)-1H-imidazole

This compound is synthesized according to a method analogous to that described in Example 1.
MH+ experimental=388.20; MH+ theoretical=387.39
Melting point: 187-189° C.

EXAMPLE 16

4-(2-{4-[2-(phenoxymethyl)-1H-imidazol-4-yl]phenoxy}ethyl) morpholine

16.1) 1-[4-(2-morpholin-4-yl ethoxy)phenyl]ethanone

Sodium hydride (3.18 g; 0.0795 mol of a powder dispersed at 60%) is added at 23° C. to a solution containing 4-(2-hydroxyethyl)morpholine (9.40 g, 0.072 mol) in dimethylformamide (60 ml). Stirring is maintained for 30 minutes then the compound 4-fluoroacetophenone (5 g, 0.0362 mol) is added. The reaction medium is stirred for one hour at 23° C. then cooled down to 0° C. and water is added. After the addition of ethyl acetate then extraction, the organic phase is washed with a saturated sodium chloride solution, dried over sodium sulphate then the solvent is evaporated off. The residue obtained is adsorbed on silica then purified by chromatography on a Biotage-type silica column (eluent: ethyl acetate-heptane: 6-1). An orange-coloured oil is obtained.

NMR $^1$H (δ ppm, DMSO): 2.34-2.54 (m, 7H); 2.66-2.71 (m, 2H); 3.57-3.71 (m, 4H); 4.16-4.19 (m, 2H); 6.97-7.07(d, 2H); 7.84-7.92 (d, 2H)

16.2) 2-bromo-1-[4-(2-morpholin-4-ylethoxy)phenyl]ethanone hydrochloride 1.02 ml of bromine (0.0205 mol) is added dropwise, under argon, to a solution cooled down to 0° C. of 1-[4-(2-morpholin-4-ylethoxy)phenyl]ethanone (4.09 g; 0.0164 mol) in ethanol (65 ml). The reaction medium is then stirred for 30 minutes at 23° C. then the solvent and the traces of bromine are evaporated in a rotary evaporator under vacuum. The residue is then stirred in diethyl ether with a few drops of ethanol. The solid obtained is filtered then dried. A beige-coloured powder is obtained.

NMR $^1$H (δ ppm, DMSO): 2.34-2.54 (m, 3H); 2.66-2.71 (m, 2H); 3.57-3.71 (m, 4H); 4.16-4.19 (m, 2H); 4.84 (s, 2H); 6.97-7.07 (d, 2H); 7.84-7.92 (d, 2H); 10 (narrow s, 1H)

16.3) 4-(2-{4-[2-(phenoxymethyl)-1H-imidazol-4-yl]phenoxy}ethyl)morpholine

The operating method is analogous to that described in Example 1.3 using as starting product 2-bromo-1-[4-(2-morpholin-4-ylethoxy)phenyl]ethanone hydrochloride described above and using one equivalent of caesium carbonate.

NMR $^1$H (δ ppm, DMSO): 2.46-2.50 (m, 4H); 2.66-2.69 (m, 2H); 3.56-3.58 (m, 4H); 4.06-4.09 (m, 2H); 5.04 (s, 2H); 6.90-7.68 (m, 10H); 12.50 (broad s, 1H) MH+ experimental=380.20; MH+ theoretical=379.46. Melting point: 144-146° C.

EXAMPLE 17

1-(2-{4-[2-(phenoxymethyl)-1H-imidazol-4-yl]phenoxy}ethyl)piperidine hydrochloride This compound is synthesized according to a method analogous to that described in Example 16.
MH+ experimental=378.30; MH+ theoretical=377.48
Melting point: 227-229° C.

EXAMPLE 18

N,N-dimethyl-N-(2-{4-[2-(phenoxymethyl)-1H-imidazol-4-yl]phenoxy}ethyl) amine hydrochloride This compound is synthesized according to a method analogous to that described in Example 16.
MH+ experimental=338.30; MH+ theoretical=337.42
Melting point: 206-208° C.

EXAMPLE 19

4-[4-(2-methoxyethoxy)phenyl]-2-(phenoxymethyl)-1H-imidazole

This compound is synthesized according to a method analogous to that described in Example 16.
MH+ experimental=325.20; MH+ theoretical=324.38
Melting point: 159-161° C.

EXAMPLE 20

2-(phenoxymethyl)-4-[4-(4,4,4-trifluorobutoxy)phenyl]-1H-imidazole

This compound is synthesized according to a method analogous to that described in Example 16.
MH+ experimental=377.20; MH+ theoretical=376.38
Melting point: 194-196° C.

EXAMPLE 21

4-[4-(4-fluorophenoxy)phenyl]-5-methyl-2-(phenoxymethyl)-1H-imidazole

21.1) 1-[4-(4-fluorophenoxy)phenyl]propan-1-one

This compound is synthesized according to a method analogous to that described in Example 1.1.

21.2) 2-bromo-1-[4-(4-fluorophenoxy)phenyl]propan-1-one

This compound is synthesized according to a method analogous to that described in Example 1.2.

21.3) 4-[4-(4-fluorophenoxy)phenyl]-5-methyl-2-(phenoxymethyl)-1H-imidazole 620 mg of 2-phenoxyethanimidamide hydrochloride (0.00333 mol) are desalified in dichloromethane by the action of a 3N sodium hydroxide solution. After decantation and extraction of the aqueous phase by dichloromethane, the organic phase is dried over sodium sulphate then evaporated to dryness. The white powder obtained is solubilized in dimethylformamide (30 ml). 275 mg of 2-bromo-1-[4-(4-fluorophenoxy)phenyl]propan-1-one (0.000851 mol) is added. The mixture is heated at 50° C. for 20 hours then returned to 23° C. before adding 25 ml of water and 30 ml of ethyl acetate. After extraction with ethyl acetate, the organic phase is dried over sodium sulphate then evaporated in a rotary evaporator under vacuum. The residue obtained is adsorbed on silica then purified by chromatography on a Biotage-type silica column (eluent: ethyl acetate-heptane: 2-8). A pale yellow-coloured foam is obtained.

NMR $^1$H ($\delta$ ppm, DMSO): 2.37 (s, 3H); 5.00 (s, 2H); 6.93-7.65 (m, 13H); 12.19 (broad s, 1H) MH+ experimental=375.20; MH+ theoretical=374.41 Melting point: <40° C.

EXAMPLE 22

4-fluoro-N-{4-[2-(phenoxymethyl)-1H-imidazol-4-yl]phenyl}benzamide

22.1) 4-(4-azidophenyl)-2-(phenoxymethyl)-1H-imidazole

This compound is prepared in a manner analogous to the method described for Example 1.3 using as starting products phenoxyacetic acid (2 g; 0.01314 mol) and 4-azidophenacyl bromide (3.15 g, 0.01314 mol). A yellow-coloured powder is obtained.

MH+ experimental=292.20; MH+ theoretical=291.31.

22.2) 4-[2-(phenoxymethyl)-1H-imidazol-4-yl]aniline

In a 100 ml reactor, 549 mg of 4-(4-azidophenyl)-2-(phenoxymethyl)-1H-imidazole (0.00188 mol) are hydrogenated over 18 hours under a hydrogen pressure of 2.5 bars with a catalytic quantity of palladium adsorbed on carbon (10% by mass). After filtration on a millipore filter then rinsing with ethanol and concentration to dryness, the residue thus obtained is treated with diethyl ether. After stirring in diethyl ether, the solid is filtered. After drying a white-coloured powder is obtained.

NMR $^1$H ($\delta$ ppm, DMSO): 3-4 (broad peak, 2H); 5.10 (s, 2H); 6.57-7.42 (m, 10H); 8-9 (broad s, 1H).

22.3) 4-fluoro-N-{4-[2-(phenoxymethyl)-1H-imidazol-4-yl]phenyl}benzamide 140 mg of 4-fluoro-benzoic acid (0.001 mol) is dissolved in dichloromethane (5 ml). Oxalyl chloride (0.13 ml, 0.0015 mol) is added followed by one drop of dimethylformamide. After stirring for thirty minutes, the reaction medium is evaporated to dryness. In a 25 ml flask, 265 mg of 4-[2-(phenoxymethyl)-1H-imidazol-4-yl]aniline (0.001 mol) is dissolved in dichloromethane (5 ml). 0.15 ml of triethylamine (0.0011 mol) then the acid chloride derivative (obtained previously) diluted in 3 ml of dichloromethane is added. After stirring for 20 hours at 23° C., the reaction medium is evaporated to dryness. 30 ml of water and 30 ml of ethyl acetate are added. After decantation, the aqueous phase is extracted with ethyl acetate. The organic phase is washed with a saturated sodium chloride solution, dried over sodium sulphate and the solvent is evaporated off. The residue obtained is adsorbed on silica then purified by chromatography on a Biotage-type silica column (eluent: ethyl acetate-heptane: 4-6). A cream-coloured powder is obtained.

NMR $^1$H ($\delta$ ppm, DMSO): 5.08 (s, 2H); 6.94-8.06 (m, 14H); 10.23 (s, 1H); 12.37 (broad s, 1H) MH+ experimental=388.20; MH+ theoretical=387.41 Melting point: 224-225° C.

EXAMPLE 23

4-{4-[2-(phenoxymethyl)-1H-imidazol-4-yl]phenoxy}benzonitrile

This compound is synthesized according to a method analogous to that described in Example 1.

MH+ experimental=368.20; MH+ theoretical=367.41 Melting point: 179-181° C.

EXAMPLE 24 ethyl 4-[2-(phenoxymethyl)-1H-imidazol-4-yl]benzoate

24.1) ethyl 4-(bromoacetyl)benzoate

This compound is prepared according to a method analogous to that described in Example 1.2 using ethyl 4-acetylbenzoate (4 g, 0.020 mol) as starting compound. A cream-coloured powder is obtained.

NMR $^1$H ($\delta$ ppm, DMSO): 1.33 (t, 3H); 4.34 (q, 2H); 4.98 (s, 2H); 8.07-8.12 (m, 4H)

24.2) ethyl 4-[2-(phenoxymethyl)-1H-imidazol-4-yl]benzoate

This compound is prepared according to a method analogous to that described in Example 1.3 using ethyl 4-(bromoacetyl)benzoate (2 g, 0.0074 mol) and 2-phenoxyethanimidamide hydrochloride (1.6 g, 0.0086 mol) as starting compounds. After treatment, a white-coloured powder is obtained.

NMR $^1$H ($\delta$ ppm, DMSO): 1.32 (t, 3H); 4.31 (q, 2H); 5.27 (s, 2H); 7.00-7.36 (m, 5H); 7.93-8.07 (m, 5H) MH+ experimental=323.20; MH+ theoretical=322.36 Melting point: 133-135° C.

EXAMPLE 25 ethyl 4-{4-[2-(phenoxymethyl)-1H-imidazol-4-yl]phenoxy}benzoate

This compound is synthesized according to a method analogous to that described in Example 1.

MH+ experimental=415.20; MH+ theoretical=414.46 Melting point: 100-102° C.

EXAMPLE 26

4-{4-[4-(methylthio)phenoxy]phenyl}-2-(phenoxymethyl)-1H-imidazole

This compound is synthesized according to a method analogous to that described in Example 1.

MH+ experimental=389.10; MH+ theoretical=388.49 Melting point: 122-124° C.

EXAMPLE 27

4-{4-[4-(methylsulphonyl)phenoxy]phenyl}-2-(phenoxymethyl)-1H-imidazole

27.1) 1-{4-[4-(methylthio)phenoxy]phenyl}ethanone

This compound is prepared according to a method analogous to that described in Example 1.1 using 4-thiomethoxyphenol (10.35 g, 0.0725 mol) and 4-fluoroacetophenone (10 g, 0.0725 mol) as starting compounds. After treatment, a beige-coloured powder is obtained.

NMR $^1$H (δ ppm, DMSO): 2.49 (s, 3H); 2.53 (s, 3H); 7.03 (d, 2H); 7.07 (d, 2H); 7.34 (d, 2H); 7.96 (d, 2H)

27.2) 2-bromo-1-{4-[4-(methylthio)phenoxy]phenyl}ethanone

This compound is prepared according to a method analogous to that described in Example 1.2 using 1-{4-[4-(methylthio)phenoxy]phenyl}ethanone (11.9 g, 0.046 mol) as starting compound; A white-coloured powder is obtained.

NMR $^1$H (δ ppm, DMSO): 2.50 (s, 3H); 4.85 (s, 2H); 7.05 (d, 2H); 7.10 (d, 2H); 7.35 (d, 2H); 8.01 (d, 2H)

27.3) 4-{4-[4-(methylthio)phenoxy]phenyl}-2-(phenoxymethyl)-1H-imidazole

This compound is prepared according to a method analogous to that described in Example 1.3 using phenoxyacetic acid (3.92 g, 0.0253 mol) and 2-bromo-1-{4-[4-(methylthio)phenoxy]phenyl}ethanone (8.53 g, 0.0253 mol) as starting compounds. After treatment, a white-coloured powder is obtained.

NMR $^1$H (δ ppm, DMSO): 2.46 (s, 3H); 5.07 (s, 2H); 6.94-7.07 (m, 7H); 7.28-7.77 (m, 8H) MH+ experimental=389.10; MH+ theoretical=388.48.

27.4) 4-{4-[4-(methylsulphonyl)phenoxy]phenyl}-2-(phenoxymethyl)-1H-imidazole 207 mg of 4-{4-[4-(methylthio)phenoxy]phenyl}-2-(phenoxymethyl)-1H-imidazole (0.00053 mol) is solubilized in acetic acid. A solution of hydrogen peroxide (0.4 ml of a solution diluted to 30% in water) is added dropwise, followed by stirring for twenty hours at 23° C. then evaporation to dryness. The residue is taken up in water and ethyl acetate. After decantation, the aqueous phase is extracted with ethyl acetate. The organic phase is dried over sodium sulphate then evaporated to dryness. The residue obtained is adsorbed on silica then purified by chromatography on a Biotage-type silica column (eluent: ethyl acetate-heptane: 2-1). A white-coloured powder is obtained.

NMR $^1$H (δ ppm, DMSO): 3.18 (s, 3H); 5.09 (s, 2H); 6.90-7.33 (m, 10H); 7.65-7.91 (m, 4H); 12.43 (narrow s, 1H) MH+ experimental=421.10; MH+ theoretical=420.49. Melting point: 143-145° C.

EXAMPLE 28

4-{4-[2-(phenoxymethyl)-1H-imidazol-4-yl]phenoxy}aniline hydrochloride

28.1) 2-bromo-1-[4-(4-nitrophenoxy)phenyl]ethanone

This compound is prepared according to a method analogous to that described in Example 1.2 using 4-acetyl-4'nitrodiphenyl ether (15 g, 0.0566 mol) as starting compound; a white-coloured powder is obtained.

NMR $^1$H (δ ppm, DMSO): 4.93 (s, 2H); 7.27-7.31 (m, 4H); 8.10 (d, 2H); 8.30 (d, 2H)

28.2) 4-[4-(4-nitrophenoxy)phenyl]-2-(phenoxymethyl)-1H-imidazole

This compound is prepared according to a method analogous to that described in Example 1.3 using phenoxyacetic acid (8.14 g, 0.053 mol) and 2-bromo-1-[4-(4-nitrophenoxy)phenyl]ethanone (18 g, 0.053 mol) as starting compounds. After treatment, a beige-coloured powder is obtained.

MH+ experimental=388.20; MH+ theoretical=387.39.

28.3) 4-{4-[2-(phenoxymethyl)-1H-imidazol-4-yl]phenoxy}aniline hydrochloride In a 1 l reactor, 3.92 g of 4-[4-(4-nitrophenoxy)phenyl]-2-(phenoxymethyl)-1H-imidazole (0.0101 mol) is hydrogenated for 7 hours under a hydrogen pressure of 1.5 bars with a catalytic quantity of palladium adsorbed on carbon (10% by mass) in ethanol (50 ml) followed by filtration on a millipore filter then rinsing with ethanol. After concentration to dryness, the residue is triturated with diethyl ether and the mixture is stirred in diethyl ether then the solid is filtered. The product obtained is adsorbed on silica then purified by chromatography on a Biotage-type silica column (eluent: ethyl acetate-heptane: 5-5 to 7-3). A beige-coloured powder is obtained.

MH+ experimental=358.20; MH+ theoretical=357.41.

The solid obtained is suspended in 100 ml of ethanol. Hydrochloric acid diluted in diethyl ether (8.4 ml of a 1 N diethyl ether solution) is added to this mixture cooled down to 0° C. After stirring for an hour, the reaction medium is evaporated to dryness then taken up in diethyl ether and filtered. After drying, a beige-coloured powder is obtained.

NMR $^1$H (δ ppm, DMSO): 3.7-4 (narrow s); 5.45 (s, 2H); 7.01-7.40 (m, 11H); 7.93 (d, 2H), 8.14 (s, 1H); 11-13 (broad peak, 2H) Melting point: >300° C.

EXAMPLE 29

{4-[2-(phenoxymethyl)-1H-imidazol-4-yl]phenyl}phenyl methanone trifluoroacetate

29.1) 1-(4-benzoylphenyl)ethanone

A mixture containing 4-acetyl benzoic acid (6 g, 0.0365 mol), boronic acid (5.34 g, 0.044 mol), palladium acetate (245 mg, 0.001 mol), tricyclohexylphosphine (716 mg, 0.0025 mol) and pivalic anhydride (11.2 ml, 0.054 mol) in a volume of water-tetrahydrofuran solvents: 1.6 ml-130 ml is heated at 60° C. under argon for 20 hours. After concentration to dryness, the residue obtained is adsorbed on silica then purified by chromatography on a Biotage-type silica column (eluent: ethyl acetate-heptane: 9-1 to 8-2). A white-coloured powder is obtained.
NMR $^1$H (δ ppm, DMSO): 2.65 (s, 3H); 7.56-8.11 (m, 9H)

29.2) 1-(4-benzoylphenyl)-2-bromoethanone

This compound is prepared according to a method analogous to that described in Example 1.2 using 1-(4-benzoylphenyl)ethanone (880 mg, 0.0039 mol) as starting compound; a white-coloured powder is obtained.
NMR $^1$H (δ ppm, DMSO): 5.08 (s, 2H); 7.56-8.16 (m, 9H)

29.3) {4-[2-(phenoxymethyl)-1H-imidazol-4-yl] phenyl}phenyl methanone trifluoroacetate This compound is prepared according to a method analogous to that described in Example 21.3 using the compound 2-phenoxyethanimidamide (400 mg, 0.00266 mol) and 1-(4-benzoylphenyl)-2-bromoethanone (685 mg, 0.00226 mol) as starting compounds. After treatment and passing the residue obtained over an RP18 silica column (eluent: acetonitrile-trifluoroacetic acid 0.1 N: 5-5), a beige-coloured powder is obtained.
NMR $^1$H (δ ppm, DMSO): 3-5 (very broad peak); 5.25 (s, 2H); 6.98-8.05 (m, 15H) MH+ experimental=355.20; MH+ theoretical=354.41 Melting point: <50° C.

EXAMPLE 30

N-(4-fluorophenyl)-4-[2-(phenoxymethyl)-1H-imidazol-4-yl]benzamide trifluoroacetate 30.1) 4-acetyl-N-(4-fluorophenyl)benzamide A mixture containing 4-acetyl-benzoic acid (4 g, 0.0243 mol), 1-(3-dimethylaminopropyl)-3-ethylcarbodiimide hydrochloride (5.13 g, 0.02673 mol), triethylamine (3.7 ml, 0.02673 mol), 1-hydroxybenzotriazole (3.62 g, 0.02673 mol) and 4-fluoroaniline (2.81 ml; 0.02916 mol) in 60 ml of tetrahydrofuran is stirred for 48 hours at 23° C. The reaction medium is filtered on frit and evaporated to dryness. The residue is taken up in a mixture of solvents : ethyl acetate-water: 50-50. The precipitate is filtered on frit, washed with isopropyl ether then isopentane. After drying, a white-coloured powder is obtained.
NMR $^1$H (δ ppm, DMSO): 2.72 (s, 3H); 7.17-7.22 (m, 2H); 7.77-7.81 (m, 2H); 8.05-8.09 (m, 4H); 10.46 (s, 1H)

30.2) 4-(bromoacetyl)-N-(4-fluorophenyl)benzamide 4-acetyl-N-(4-fluorophenyl)benzamide (1.5 g, 0.00583 mol) is dissolved in 100 ml of methanol. Pyridinium tribromide resin is added (4 g of resin to 2 mmol of Br$_3$ per gram, 0.0081 mol) followed by heating for 4 hours at 40° C. The reaction medium is filtered on frit, rinsed with methanol and evaporated to dryness. A pale yellow-coloured powder is obtained.
NMR $^1$H (δ ppm, DMSO): 4.99 (s, 2H); 7.18-7.23 (m, 2H); 7.78-7.81 (m, 2H); 8.06-8.14 (m, 4H); 10.47 (s, 1H)

30.3) N-(4-fluorophenyl)-4-[2-(phenoxymethyl)-1H-imidazol-4-yl]benzamide trifluoroacetate This compound is prepared according to a method analogous to that described in Example 21.3 using 2-phenoxyethanimidamide (225 mg, 0.0015 mol) and 4-(bromoacetyl)-N-(4-fluorophenyl)benzamide (426 mg, 0.00128 mol) as starting compounds. After treatment and passing the residue obtained over an RP18 silica column (eluent: acetonitrile-trifluoroacetic acid 0.1N: 5-5), a yellow-coloured powder is obtained.
NMR $^1$H (δ ppm, DMSO): 3-4 (broad peak); 5.28 (s, 2H); 7.01-7.37 (m, 7H); 7.78-8.02 (m, 7H); 10.30 (s, 1H) MH+ experimental=388.10; MH+ theoretical=387.41 Melting point: 198-200° C.

EXAMPLE 31

4-[4-(3-nitrophenoxy)phenyl]-2-(phenoxymethyl)-1H-imidazole 31.1) 1-nitro-3-phenoxybenzene This compound is prepared according to a method analogous to that described in Example 1.1 using 1-fluoro-3-nitro benzene (15.4 g, 0.106 mol) and phenol (10 g, 0.106 mol) as starting compounds. After treatment, an orange-coloured oil is obtained.
NMR $^1$H (δ ppm, DMSO): 7.13-7.99 (m, 9H)

31.2) 1-[4-(3-nitrophenoxy)phenyl]ethanone

The compound 1-nitro-3-phenoxybenzene (10.17 g, 0.0473 mol) is put into solution in carbon disulphide (70 ml). Aluminium chloride (10.06 g, 0.076 mol) is added by portions at ambient temperature. The reaction medium is cooled down to 0° C. then acetyl chloride (2.4 ml, 0.038 mol) is added dropwise. The reaction medium is left to return to 23° C. then stirring is maintained for 5 hours, followed by cooling down again to 0° C., then the careful addition of ethyl acetate, crushed ice and 3 N hydrochloric acid. After decantation, the medium is extracted with ethyl acetate. The organic phase is washed with water, with a saturated solution of sodium carbonate then with a saturated solution of sodium chloride. It is then dried over sodium sulphate then evaporated. The residue obtained is adsorbed on silica then purified by chromatography on a Biotage-type silica column (eluent: ethyl acetate-heptane: 1-4). After washing with diethyl ether, a yellow-coloured powder is obtained.
NMR 1H (δ ppm, DMSO): 2.57 (s, 3H); 7.20 (d, 2H); 7.50-8.04 (m, 6H)

31.3) 2-bromo-1-[4-(3-nitrophenoxy)phenyl]ethanone

This compound is prepared according to a method analogous to that described in Example 1.2 using 1-[4-(3-nitrophenoxy)phenyl]ethanone (5.4 g, 0.021 mol) as starting compound; a beige-coloured powder is obtained.
NMR $^1$H (δ ppm, DMSO): 4.92 (s, 2H); 7.21-7.23 (m, 2H); 7.64-8.08 (m, 6H)

31.4) 4-[4-(3-nitrophenoxy)phenyl]-2-(phenoxymethyl)-1H-imidazole

This compound is prepared according to a method analogous to that described in Example 1.3 using phenoxyacetic acid (1.16 g, 0.0075 mol) and the compound 2-bromo-1-[4-(3-nitrophenoxy)phenyl]ethanone (2.46 g, 0.0075 mol) as starting compounds. After treatment, a beige-coloured powder is obtained.

NMR ¹H (δ ppm, DMSO): 5.08 (s, 2H); 6.94-7.87 (m, 14H); 12.45 (narrow s, 1H) MH+ experimental=388.20; MH+ theoretical=387.39. Melting point: 140-142° C.

EXAMPLE 32

3-{4-[2-(phenoxymethyl)-1H-imidazol-4-yl] phenoxy}aniline hydrochloride

In a 250 ml reactor, 4-[4-(3-nitrophenoxy)phenyl]-2-(phenoxymethyl)-1H-imidazole (0.28 g, 0.00072 mol) is hydrogenated for 1 hour under a hydrogen pressure of 1.5 bars with a catalytic quantity of palladium adsorbed on carbon (10% by mass) in ethanol (70 ml).

The reaction medium is filtered on a millipore filter then rinsed with ethanol. After concentration to dryness, the residue is triturated with diethyl ether, then stirred in a mixture of diethyl ether and isopentane (1:9) and finally the solid is filtered. After drying, a yellow-coloured powder is obtained which is purified by chromatography on an RP18 silica column (eluent: 0.1N acetonitrile-trifluoroacetic acid: 1-2).

NMR ¹H (δ ppm, DMSO): 3-4 (narrow s); 5.30 (s, 2H); 6.21-6.26 (m, 2H); 6.39 (d, 1H); 7.01-7.09 (m, 6H); 7.33-7.37 (m, 2H); 7.76-7.78 (m, 2H); 7.92 (s, 1H) MH+ experimental=358.20; MH+ theoretical=357.41

The solid obtained in the preceding stage (0.07 g, 0.00020 mol) is stirred for 30 minutes in a mixture of ethyl acetate and a saturated solution of sodium hydrogen carbonate, followed by decanting, then the organic phase is washed with a saturated solution of sodium carbonate, dried over sodium sulphate then evaporated. The residue is taken up in ethanol (7 ml) then, at 0° C., a 1 N hydrochloric acid solution in diethyl ether (0.43 ml, 0.00044 mol) is added. After stirring for 30 minutes, the reaction medium is evaporated to dryness then taken up in diethyl ether and filtered. After drying, a beige-coloured powder is obtained.

NMR ¹H (δ ppm, DMSO): 3-4 (narrow s); 5.44 (s, 2H); 6.67 (narrow s, 2H); 6.80 (narrow s, 1H); 7.02-7.38 (m, 8H); 7.89-7.91 (m, 2H); 8.14 (s, 1H) MH+ experimental=358.20; MH+ theoretical=357.41 Melting point: >300° C.

EXAMPLE 33

4-{4-[4-(benzyloxy)phenoxy]phenyl}-2-(phenoxymethyl)-1H-imidazole

This compound is synthesized according to a method analogous to that described in Example 1.

MH+ experimental=449.20; MH+ theoretical=448.52 Melting point: 134-136° C.

EXAMPLE 34

4-{4-[2-(phenoxymethyl)-1H-imidazol-4-yl] phenoxy}phenol 34.1) 4-{4-[4-(benzyloxy)phenoxy]phenyl}-2-(phenoxymethyl)-1H-imidazole This compound is prepared according to a method analogous to that described in Example 1.3 using phenoxyacetic acid (1.82 g, 0.012 mol) and 1-{4-[4-(benzyloxy)phenoxy] phenyl}-2-bromoethanone (4.76 g, 0.012 mol) as starting products. After treatment, a beige-coloured powder is obtained.

NMR ¹H (δ ppm, DMSO): 5.07 (s, 4H); 6.89-7.75 (m, 19H); 12.38 (s, 1H) MH+ experimental=449.20; MH+ theoretical=448.5.

34.2) 4-{4-[2-(phenoxymethyl)-1H-imidazol-4-yl] phenoxy}phenol

In a 100 ml reactor, 138 mg of 4-{4-[4-(benzyloxy)phenoxy]phenyl}-2-(phenoxymethyl)-1H-imidazole (0.0003 mol) in 10 ml of ethanol with a catalytic quantity of palladium adsorbed on carbon (10% by mass), are hydrogenated for 24 hours under a hydrogen pressure of 4 bars. The reaction medium is filtered on a millipore filter then rinsed with ethanol and evaporated to dryness. The residue is triturated with diethyl ether and the mixture is stirred in diethyl ether and the solid is filtered. The product obtained is adsorbed on silica then purified by chromatography on a Biotage-type silica column (eluent: ethyl acetate-heptane: 2-8 to 5-5). After washing with diethyl ether, a white-coloured powder is obtained.

NMR ¹H (δ ppm, DMSO): 5.06 (s, 2H); 6.76-7.70 (m, 14H); 9.34 (s, 1H); 12.41 (narrow s, 1H) MH+ experimental=359.20; MH+ theoretical=358.39 Melting point: 211-213° C.

EXAMPLE 35

4-[4-(3-fluorophenoxy)phenyl]-2-(phenoxymethyl)-1H-imidazole

This compound is synthesized according to a method analogous to that described in Example 1.

MH+ experimental=361.20; MH+ theoretical=360.39 Melting point: 177-179° C.

EXAMPLE 36

N-(4-{4-[2-(phenoxymethyl)-1H-imidazol-4-yl] phenoxy}phenyl) acetamide

4-{4-[2-(phenoxymethyl)-1H-imidazol-4-yl] phenoxy}aniline (600 mg, 0.00168 mol), (prepared according to a method analogous to that described in Example 28) is suspended in ethanol (30 ml) at 0° C. Triethylamine (0.235 ml, 0.00168 mol) and methyl iodide (0.136 ml, 0.0022 mol) are added. The mixture is stirred for 20 hours then evaporated to dryness. The residue obtained is adsorbed on silica then purified by chromatography on a Biotage-type silica column (eluent: ethyl acetate-heptane: 4-6 to 5-5). After washing with diethyl ether and isopentane, a beige-coloured powder is obtained.

NMR ¹H (δ ppm, DMSO): 2.66 (s, 3H); 5.06 (s, 2H); 5.54 (narrow s, 1H); 6.54-7.70 (m, 14H); 12.32 (narrow s, 1H) MH+ experimental=372.30; MH+ theoretical=371.44 Melting point: 176-177° C.

EXAMPLE 37

2-nitro-4-{4-[2-(phenoxymethyl)-1H-imidazol-4-yl] phenoxy}aniline trifluoroacetate This compound is synthesized according to a method analogous to that described in Example 1.

MH+ experimental=403.20; MH+ theoretical=402.41 Melting point: 178-180° C.

EXAMPLE 38

N-methyl-N-(4-{4-[2-(phenoxymethyl)-1H-imidazol-4-yl]phenoxy}phenyl) amine

4-{4-[2-(phenoxymethyl)-1H-imidazol-4-yl]phenoxy}aniline (238 mg, 0.0066 mol), (prepared according to a method analogous to that described in Example 28) is suspended in dichloromethane (5 ml) at 23° C. Triethylamine (0.1 ml, 0.0079 mol) and acetic anhydride (0.062 ml, 0.0066 mol) are added. The mixture is then stirred for 20 hours then evaporated to dryness. The oil obtained is taken up with ethyl acetate and water. After decantation and extraction by ethyl acetate, the organic phase is washed with water then with a saturated solution of sodium chloride, dried over sodium sulphate then the solvent is evaporated off. The residue obtained is adsorbed on silica then purified by chromatography on a Biotage-type silica column (eluent: ethyl acetate-heptane: 7-3 to 9-1). After washing with diisopropyl ether and isopentane, a beige-coloured powder is obtained.

NMR $^1$H ($\delta$ ppm, DMSO): 2.03 (s, 3H); 5.08 (s, 2H); 6.94-7.74 (m, 14H); 9.92 (s, 1H); 12.32 (narrow s, 1H) MH+ experimental=400.30; MH+ theoretical=399.44 Melting point: 125-126° C.

EXAMPLE 39

3-{4-[2-(phenoxymethyl)-1H-imidazol-4-yl]phenoxy}benzonitrile

This compound is synthesized according to a method analogous to that described in Example 1.

MH+ experimental=368.30; MH+ theoretical=367.41 Melting point: 161-163° C.

EXAMPLE 40

4-[4-(2-nitrophenoxy)phenyl]-2-(phenoxymethyl)-1H-imidazole

This compound is synthesized according to a method analogous to that described in Example 31.

MH+ experimental=388.20; MH+ theoretical=387.39 Melting point: 128-129° C.

EXAMPLE 41

2-{4-[2-(phenoxymethyl)-1H-imidazol-4-yl]phenoxy}aniline hydrochloride

This compound is synthesized according to a method analogous to that described in Example 31.

MH+ experimental=358.30; MH+ theoretical=357.41 Melting point: 88-89° C.

EXAMPLE 42

1-(4-{4-[2-(phenoxymethyl)-1H-imidazol-4-yl]phenoxy}phenyl)methanamine hydrochloride In a 100 ml reactor, 120 mg of 4-{4-[2-(phenoxymethyl)-1H-imidazol-4-yl]phenoxy}benzonitrile (0.00033 mol) (obtained according to a method analogous to that described in Example 1) in ethanol (10 ml) in the presence of evaporated hydrochloric acid (0.1 ml) and a catalytic quantity of palladium adsorbed on carbon (10% by mass), are hydrogenated for two days under a hydrogen pressure of 1.5 bars. The reaction medium is filtered on a millipore filter then rinsed with ethanol, evaporated to dryness and the residue is triturated with a mixture of solvents such as diethyl ether and ethanol in a proportion of 1-1. After drying a green-coloured powder is obtained.

NMR $^1$H ($\delta$ ppm, DMSO): 4.00 (m, 2H); 5.36 (s, 2H); 7.00-8.32 (m, 17H) MH+ experimental=372.30; MH+ theoretical=371.44 Melting point: >300° C.

EXAMPLE 43

1-(3-{4-[2-(phenoxymethyl)-1H-imidazol-4-yl]phenoxy}phenyl)methanamine hydrochloride This compound is synthesized according to a method analogous to that described in Example 42.

MH+ experimental=272.30; MH+ theoretical=271.44 Melting point: 200-202° C.

EXAMPLE 44

4-[4-(3-bromophenoxy)phenyl]-2-(phenoxymethyl)-1H-imidazole

This compound is synthesized according to a method analogous to that described in Example 1.

MH+ experimental=421.10; MH+ theoretical=421.29 Melting point: 133-135° C.

EXAMPLE 45

2-fluoro-4-{4-[2-(phenoxymethyl)-1H-imidazol-4-yl]phenoxy}aniline hydrochloride 45.1) 4-amino-3-fluorophenol In a 1 l reactor, 10 g of 4-nitro-3-fluorophenol (0.0637 mol) with a catalytic quantity of palladium adsorbed on carbon (10% by mass) in ethanol (250 ml) is hydrogenated for 2 hours under a hydrogen pressure of 1.5 bars. The reaction medium is then filtered on a millipore filter then rinsed with ethanol, followed by evaporation to dryness and the residue is triturated with diethyl ether and the reaction medium stirred in a mixture of diisopropyl ether and isopentane (1:4). After filtration of the solid and drying, a beige-coloured powder is obtained.

NMR $^1$H ($\delta$ ppm, DMSO): 4.35 (s, 2H); 6.32-6.61 (m, 3H); 8.75 (s, 1H)

45.2) 1-[4-(4-amino-3-fluorophenoxy)phenyl]ethanone

This compound is prepared according to a method analogous to that described in Example 1.1 using 4-amino-3-fluorophenol (7.68 g, 0.06 mol) and 4-fluoroacetophenone (8.34 g, 0.06 mol) as starting compounds. After treatment, a white-coloured powder is obtained.

NMR $^1$H ($\delta$ ppm, DMSO): 2.51 (s, 3H); 5.10 (s, 2H); 6.69-6.96 (m, 5H); 7.92 (d, 2H)

45.3) 1-[4-(4-amino-3-fluorophenoxy)phenyl]-2-bromoethanone hydrochloride

This compound is prepared according to a method analogous to that described in Example 1.2 using 1-[4-(4-amino-3-fluorophenoxy) phenyl]ethanone (4 g, 0.0163 mol) as starting compound; a pink-coloured powder is obtained.

NMR $^1$H (δ ppm, DMSO): 4.84 (s, 2H); 5-6 (broad peak); 6.99-7.13 (m, 5H); 7.93-8.02 (m, 2H)

45.4) 2-fluoro-4-{4-[2-(phenoxymethyl)-1H-imidazol-4-yl]phenoxy}aniline hydrochloride This compound is prepared according to a method analogous to that described in Example 1.3 using phenoxyacetic acid (1.6 g, 0.0106 mol), and 1-[4-(4-amino-3-fluorophenoxy)phenyl]-2-bromoethanone hydrochloride (4.2 g, 0.0106 mol) and caesium carbonate (3.44 g, 0.0106 mol) as starting compounds. After treatment, a beige-coloured powder is obtained.

MH+ experimental=376.20; MH+ theoretical=375.4

The solid obtained (0.06 g, 0.00016 mol) is suspended in 7 ml of ethanol. 0.35 ml of a 1 N hydrochloric acid solution in diethyl ether (0.00032 mol) is poured into this mixture cooled down to 0° C. After stirring for one hour at this temperature, the reaction medium is evaporated to dryness then taken up in diethyl ether and filtered. After drying, a pink-coloured powder is obtained.

NMR $^1$H (δ ppm, DMSO): 3-5 (broad peak); 5.44 (s, 2H); 6.77-6.80 (m, 1H); 6.97-7.12 (m, 7H); 7.34-7.38 (m, 2H); 7.86 (d, 2H); 8.11 (s, 1H) Melting point: >300° C.

EXAMPLE 46

4-[4-(3-chlorophenoxy)phenyl]-2-(phenoxymethyl)-1H-imidazole

This compound is synthesized according to a method analogous to that described in Example 1.
MH+ experimental=377.20; MH+ theoretical=376.84 Melting point: 146-148° C.

EXAMPLE 47

4-[4-(3,5-difluorophenoxy)phenyl]-2-(phenoxymethyl)-1H-imidazole

This compound is synthesized according to a method analogous to that described in Example 1.
MH+ experimental=379.10; MH+ theoretical=378.38 Melting point: 160-161° C.

EXAMPLE 48

4-(4-benzylphenyl)-2-(phenoxymethyl)-1H-imidazole

This compound is synthesized according to a method analogous to that described in Example 31.
MH+ experimental=341.20; MH+ theoretical=340.42 Melting point: 147-148° C.

EXAMPLE 49

4-[4-(3-methylphenoxy)phenyl]-2-(phenoxymethyl)-1H-imidazole

This compound is synthesized according to a method analogous to that described in Example 1.
MH+ experimental=357.20; MH+ theoretical=356.42 Melting point: 160-162° C.

EXAMPLE 50

4-[4-(2-chlorophenoxy)phenyl]-2-(phenoxymethyl)-1H-imidazole hydrochloride

This compound is synthesized according to a method analogous to that described in Example 1.
MH+ experimental=377.10; MH+ theoretical=376.84 Melting point: 158-160° C.

EXAMPLE 51

4-[4-(2-fluorophenoxy)phenyl]-2-(phenoxymethyl)-1H-imidazole

This compound is synthesized according to a method analogous to that described in Example 1.
MH+ experimental=361.10; MH+ theoretical=360.39 Melting point: 154-156° C.

EXAMPLE 52

4-[4-(3,4-difluorophenoxy)phenyl]-2-(phenoxymethyl)-1H-imidazole

This compound is synthesized according to a method analogous to that described in Example 1.
MH+ experimental=379.1 0; MH+ theoretical=378.38 Melting point: 188-190° C.

EXAMPLE 53

$N^1$-(4-{4-[2-(phenoxymethyl)-1H-imidazol-4-yl]phenoxy}phenyl)glycinamide hydrochloride 53.1) tert-butyl {2-oxo-2-[(4-{4-[2-(phenoxymethyl)-1H-imidazol-4-yl]phenoxy}phenyl)amino]ethyl}carbamate A mixture containing terbutoxycarbonyl N-glycine acid (417 mg, 0.00238 mol), 1-(3-dimethylaminopropyl)-3-ethyl-carbodiimide hydrochloride (1 g, 0.00524 mol), triethylamine (0.73 ml, 0.00524 mol), 1-hydroxybenzotriazole (354 mg, 0.00262 mol) and {4-[2-(phenoxymethyl)-1H-imidazol-4-yl]phenoxy}aniline (850 mg, 0.00238 mol, prepared according to Example 28) in 15 ml of dimethylformamide and 3 ml of dichloromethane is stirred for 24 hours at 23° C. The reaction medium is evaporated to dryness then the oil obtained is taken up in ethyl acetate and water. After decantation and extraction with ethyl acetate, the organic phase is washed with water then with a saturated solution of sodium chloride, dried over sodium sulphate then the solvent is evaporated off. The residue obtained is adsorbed on silica then purified by chromatography on a Merck-type silica column (eluent: dichloromethane-methanol: 98-2 to 95-5). After washing with diisopropyl ether and isopentane, an orange-coloured powder is obtained.

NMR $^1$H (δ ppm, DMSO): 1.38 (s, 9H); 3.69-3.71 (m, 2H); 5.07 (s, 2H); 6.94-7.45 (m, 15H); 9.92 (s, 1H); 12.3-12.4 (narrows, 1H) MH+ experimental=515.30; MH+ theoretical=514.56

53.2) N1-(4-{4-[2-(phenoxymethyl)-1H-imidazol-4-yl]phenoxy}phenyl)glycinamide hydrochloride The compound tert-butyl {2-oxo-2-[(4-{4-[2-(phenoxymethyl)-1H-imidazol-4-yl]phenoxy}phenyl)amino]

ethyl}carbamate (331 mg, 0.00064 mol) in 6 ml of ethyl acetate is stirred for 2 hours at 23° C. then evaporated to dryness. After washing with ether and isopentane, after filtration and drying, a beige-coloured powder is obtained.

NMR $^1$H (δ ppm, DMSO): 3.3-3.7 (narrow s, 3H); 3.74-3.80 (m, 2H); 5.43 (s, 2H); 7.01-8.26 (m, 16H); 10.84 (s, 1H) MH+ experimental=415.20; MH+ theoretical=414.46 Melting point: >250° C.

EXAMPLE 54

4-[4-(2,5-difluorophenoxy)phenyl]-2-(phenoxymethyl)-1H-imidazole

This compound is synthesized according to a method analogous to that described in Example 1.
MH+ experimental=379.20; MH+ theoretical=378.38 Melting point: 128-130° C.

EXAMPLE 55

4-[4-(2,4-difluorophenoxy)phenyl]-2-(phenoxymethyl)-1H-imidazole

This compound is synthesized according to a method analogous to that described in Example 1.
MH+ experimental=379.20; MH+ theoretical=378.38 Melting point: 131-133° C.

EXAMPLE 56

4-[4-(2,3-difluorophenoxy)phenyl]-2-(phenoxymethyl)-1H-imidazole

This compound is synthesized according to a method analogous to that described in Example 1.
MH+ experimental=379.00; MH+ theoretical=378.38 Melting point: 127-129° C.

EXAMPLE 57

4-[4-(2,6-difluorophenoxy)phenyl]-2-(phenoxymethyl)-1H-imidazole

This compound is synthesized according to a method analogous to that described in Example 1.
MH+ experimental=379.00; MH+ theoretical=378.38 Melting point: 143-145° C.

According to a method analogous to that described in Examples 1 to 57, the following compounds can also be prepared:

N-{4-[2-(phenoxymethyl)-1H-imidazol-4-yl]phenyl}pyridin-4-amine;
4-{4-[2-(phenoxymethyl)-1H-imidazol-4-yl]phenoxy}pyridine;
4-({4-[2-(phenoxymethyl)-1H-imidazol-4-yl]phenyl}thio)pyridine;
N-{4-[2-(phenoxymethyl)-1H-imidazol-4-yl]phenyl}-N-phenylamine;
N-{4-[2-(phenoxymethyl)-1H-imidazol-4-yl]phenyl}pyrimidin-2-amine;
2-(phenoxymethyl)-4-[4-(3,4,5-trimethoxyphenoxy)phenyl]-1H-imidazole;
N-{4-[2-(phenoxymethyl)-1H-imidazol-4-yl]phenyl}-1H-indol-4-amine;
N-{4-[2-(phenoxymethyl)-1H-imidazol-4-yl]phenyl}-1H-indol-6-amine;
N-{4-[2-(phenoxymethyl)-1H-imidazol-4-yl]phenyl}pyrazin-2-amine;
N-{4-[2-(phenoxymethyl)-1H-imidazol-4-yl]phenyl}-4H-1,2,4-triazol-4-amine;
N-{4-[2-(phenoxymethyl)-1H-imidazol-4-yl]phenyl}furan-2-amine;
N-{4-[2-(phenoxymethyl)-1H-imidazol-4-yl]phenyl}furan-3-amine;
N-{4-[2-(phenoxymethyl)-1H-imidazol-4-yl]phenyl}-N-thien-2-ylamine; or a pharmaceutically acceptable salt thereof.

Pharmacoloiical Study

The affinity of the compounds of the present invention is determined by using the following experimental procedure:

The different cell lines are incubated at 37° C. in an atmosphere containing 5% of $CO_2$ (Format Scientifique incubators) in DMEM (Dulbecco's Modified Eagle Medium) with 4.5 g/l of glucose to which 10% heat-inactivated calf serum, 50 U/ml of penicillin, 50 μg/ml of streptomycin and 2 mM of glutamine (Gibco) are added.

The cell proliferation inhibition is measured by the colorimetric test with WST (tetrazolium salt, Boehringer Mannheim, Meylan, France). The cells are seeded in 96-well microplates (TPP) at a rate of 2000 cells per well for the HT29s, 1300 for the DU145s and 1200 for the MIA-Pa-Ca-2s in 95 μl of culture medium. 24 hours after seeding, 5 μl of drugs are added at different concentrations (the product is dissolved in $10^{-2}$M DMA then it is diluted in culture medium). The final concentrations range from 25 μM to 0.5 μM. After incubation for 72 hours, 10 μl of WST per well is added and determination of the absorbance is carried out at 450 nM 2 hours later (Victor, Perkin Elmer).

Each experiment is carried out twice and is the result of the absorbance measurement of eight wells. For each product, measurement of the $IC_{50}$ corresponding to the concentration of the product which leads to 50% inhibition of cell growth, is determined by a linear regression calculation (linear deviation, deviation of the linearity and difference between the experiments, TSAR calculation program) on the linear part of the sigmoid.

The $IC_{50}$ values obtained for the majority of the compounds vary from 1 μM to 10 nM.

The invention claimed is:
1. A compound of the formula

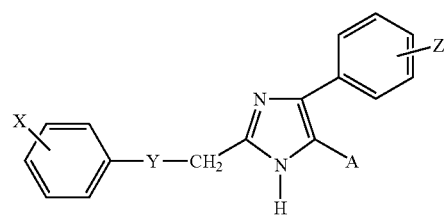

I in racemic, enantiomeric form or any combinations of these forms wherein:
X is at least one H or halo;
Y is —O— or —S—;
A is H or $(C_1$-$C_6)$alkyl;
Z is selected from the group consisting of:
$(C_1$-$C_6)$alkyl optionally substituted by at least one halo;
aryl optionally substituted by at least one member selected from the group consisting of: halo, nitro, cyano, hydroxy, $(C_1$-$C_6)$alkyl optionally substituted by at least one halo, —(CH$_2$)$_n$—NR$_3$R$_4$, (C$_1$-C$_6$)alkyl-sulfonyl, (C$_1$-C$_6$)alkyl-thio, (C$_1$-C$_6$)alkoxy optionally substituted by at least one halo, (C$_1$-C$_6$)alkoxy-carbonyl, phosphate, sulfate, glycoside and —NH—C(O)—CH(R$_A$)—NR$_5$R$_6$;

aryl-(C$_1$-C$_6$)alkyl;

heteroaryl;

Z$_1$-Z'$_1$;

—NR$_N$—C(O)-Z'$_2$ and

-Z$_2$-Z'$_2$;

Z$_1$ is selected from the group consisting of —O—, —C(O)—O—, —NR$_N$—C(O)— and —C(O)—NR$_N$—;

Z'$_1$ is selected from the group consisting of (C$_1$-C$_{10}$)alkyl; aryl-(C$_1$-C$_6$)alkyl, the aryl of which is optionally substituted by at least one halo; and (C$_1$-C$_6$)alkyl substituted by at least one member selected from the group consisting of halo, (C$_1$-C$_6$)alkoxy, (C$_1$-C$_6$)alkylthio and —NR$_1$R$_2$;

R$_1$ and R$_2$ are, independently, H or (C$_1$-C$_6$)alkyl, or form together with the nitrogen atom to which they are attached, a heterocycloalkyl optionally substituted by (C$_1$-C$_6$)alkyl;

Z$_2$ is selected from the group consisting from —O—, —S—, —SO$_2$—, —C(O)—, —C(O)—NR$_N$— and —NR$_N$—;

Z'$_2$ is an aryl or heteroaryl, the aryl and heteroaryl being optionally substituted by at least one member selected from the group consisting of:

halo, nitro, cyano, hydroxy, (C$_1$-C$_6$)alkyl optionally substituted by at least one halo, (C$_1$-C$_6$)alkyl-thio, (C$_1$-C$_6$)alkyl-sulfonyl, (C$_1$-C$_6$)alkoxy optionally substituted by at least one halo, aryl-alkoxy, (C$_1$-C$_6$)alkoxy-carbonyl, phosphate, sulfate, glycoside, —(CH$_2$)$_n$—NR$_3$R$_4$ and —NH—C(O)—CH(R$_A$)—NR$_5$R$_6$;

R$_3$ and R$_4$ are, independently, selected from the group consisting of H or (C$_1$-C$_6$)alkyl, (C$_1$-C$_6$)alkyl-carbonyl and (C$_1$-C$_6$)alkyl-sulfonyl, or R$_3$ and R$_4$ form together with the nitrogen atom to which they are attached, a heteroaryl or a heterocycloalkyl optionally substituted by (C$_1$-C$_6$)alkyl;

R$_5$ and R$_6$ are, independently, H or (C$_1$-C$_6$)alkyl;

R$_A$ is the residue of an amino acid of the formula NH$_2$—CH(R$_A$)—C(O)—OH;

R$_N$ is hydrogen or (C$_1$-C$_6$)alkyl;

n is an integer from 0 to 3; or a pharmaceutically acceptable salt thereof except compounds in which A is hydrogen and Z is -3-CF$_3$.

2. A compound of claim 1, wherein

X is H or halo;

Y is —O— or —S—;

A is H or (C$_1$-C$_6$)alkyl;

Z is selected from the group consisting of:

(C$_1$-C$_6$)alkyl optionally substituted by at least one halo;

aryl optionally substituted by at least one member selected from the group consisting of: halo, nitro, cyano, hydroxy, (C$_1$-C$_6$)alkyl optionally substituted by at least one halo, and (C$_1$-C$_6$)alkoxy optionally substituted by at least one halo;

heteroaryl;

Z$_1$-Z'$_1$;

—NH—C(O)-Z'$_2$; and

Z$_2$-Z'$_2$;

Z$_1$ is selected from the group consisting of —O—, —N—C(O)— and —C(O)—NH—;

Z'$_1$ is selected from the group consisting of (C$_4$-C$_{10}$)alkyl; aryl-(C$_1$-C$_6$)alkyl, the aryl of which is optionally substituted by at least one halo and (C$_1$-C$_6$)alkyl substituted by at least one member selected from the group consisting of halo, (C$_1$-C$_6$)alkoxy, (C$_1$-C$_6$)alkylthio and —NR$_1$R$_2$;

R$_1$ and R$_2$ are, independently, H or (C$_1$-C$_6$)alkyl, or form together with the nitrogen atom to which they are attached, a heterocycloalkyl optionally substituted by (C$_1$-C$_6$)alkyl;

Z$_2$ is selected from the group consisting of —O—, —S—, —SO$_2$—, —C(O)— or —C(O)—NH—;

Z'$_2$ is aryl optionally substituted by at least one member selected from the group consisting of: halo, nitro, cyano, hydroxy, (C$_1$-C$_6$)alkyl optionally substituted by at least one halo, and (C$_1$-C$_6$)alkoxy optionally substituted by at least one halo; or a pharmaceutically acceptable salt thereof.

3. A compound of claim 1 wherein A is H and Y is —O—; or a pharmaceutically acceptable salt thereof.

4. A compound of claim 1 wherein X is H; or a pharmaceutically acceptable salt thereof.

5. A compound of claim 4, wherein

Z is at least one member, in meta and/or para position and selected from heteroaryl or Z$_2$-Z'$_2$;

Z$_2$ is selected from the group consisting of —O—, —S—, —SO$_2$—, —C(O)— and —C(O)—NH—;

Z'$_2$ is phenyl of naphthyl optionally substituted by at least one member selected from the group consisting of halo, nitro, cyano, hydroxy, (C$_1$-C$_6$)alkyl optionally substituted by at least one halo, and (C$_1$-C$_6$)alkoxy optionally substituted by at least one halo; or a pharmaceutically acceptable salt thereof.

6. A compound of claim 1, Z is selected from the group consisting of:

heteroaryl;

Z$_1$-Z'$_1$ wherein either Z$_1$ is selected from the group consisting of —O—, —NR$_N$—C(O)— or —C(O)—NR$_N$— and Z'$_1$ benzyl;

or Z$_1$ is selected from the group consisting of —O—, —C(O)—O—, —NR$_N$—C(O)— or —C(O)—NR$_N$— and Z'$_1$ is (C$_1$-C$_6$)alkyl substituted by at least one member selected from the group consisting of: halo, (C$_1$-C$_6$)alkoxy, (C$_1$-C$_6$)alkylthio and —NR$_1$R$_2$;

R$_1$ and R$_2$ are, independently, H or (C$_1$-C$_6$)alkyl, or form together with the nitrogen atom to which they are attached, a heterocycloalkyl;

Z$_2$-Z'$_2$ wherein

Z$_2$ is selected from the group consisting of —O—, —S—, —SO$_2$—, —C(O)—, —C(O)—NR$_N$— and —NR$_N$—;

Z'$_2$ is phenyl or phenyl substituted by at least one member selected from the group consisting of:

halo, nitro, cyano, hydroxy, (C$_1$-C$_6$)alkyl optionally substituted by at least one halo, (C$_1$-C$_6$)alkyl-thio, (C$_1$-C$_6$)alkyl-sulfonyl, (C$_1$-C$_6$)alkoxy optionally substituted by at least one halo, aryl-alkoxy, C$_1$-C$_6$)alkoxy-carbonyl, —(CH$_2$)$_n$—NR$_3$R$_4$ and —NH—C(O)—CH(R$_A$)—NR$_5$R$_6$;

R$_3$ and R$_4$ are, independently, selected from the group consisting of H or (C$_1$-C$_6$)alkyl and (C$_1$-C$_6$)alkyl-carbonyl;

R$_5$ and R$_6$ are, independently, H or (C$_1$-C$_6$)alkyl;

R$_A$ is the residue of an amino acid of the formula NH$_2$—CH(R$_A$)—C(O)—OH;

R$_N$ is hydrogen or (C$_1$-C$_6$)alkyl; or a pharmaceutically acceptable salt thereof.

7. A compound of claim 1, wherein Z is -$Z_2$-$Z'_2$; or a pharmaceutically acceptable salt thereof.

8. A compound of claim 7, wherein Z is in meta and/or para position; or a pharmaceutically acceptable salt thereof.

9. A compound of claim 7, wherein $Z_2$ is selected from the group consisting of —O—, —S—, —$SO_2$— and —C(O)—; or a pharmaceutically acceptable salt thereof.

10. A compound of claim 9, wherein $Z_2$ is —O—; or a pharmaceutically acceptable salt thereof.

11. A compound of claim 7, wherein $Z_2$ is —$NR_N$—; or a pharmaceutically acceptable salt thereof.

12. A compound of claim 7, wherein
$Z'_2$ is phenyl or phenyl substituted by at least one member selected from the group consisting of:
halo, nitro, cyano, hydroxy, ($C_1$-$C_6$)alkyl optionally substituted by at least one halo, ($C_1$-$C_6$)alkyl-thio, ($C_1$-$C_6$)alkyl-sulfonyl, ($C_1$-$C_6$)alkoxy optionally substituted by at least one halo, benzyloxy, ($C_1$-$C_6$) alkoxy-carbonyl, phosphate, —$(CH_2)_n$—$NR_3R_4$ and —NH—C(O)—CH($R_A$)—$NR_5R_6$;
$R_3$ and $R_4$ are, independently, selected from the group consisting of H, ($C_1$-$C_6$)alkyl, ($C_1$-$C_6$)alkyl-carbonyl and ($C_1$-$C_6$)alkyl-sulfonyl:
$R_N$ is hydrogen or ($C_1$-$C_6$)alkyl;
$R_5$ and $R_6$ are, independently, H or ($C_1$-$C_6$)alkyl; and
$R_A$ is the residue of an amino acid of the formula $NH_2$—CH($R_A$)—C(O)—OH; or a pharmaceutically acceptable salt thereof.

13. A compound of claim 7, wherein
$Z'_2$ is phenyl substituted by at least one member selected from the group consisting of: halo, nitro, cyano, hydroxy, ($C_1$-$C_6$)alkyl-sulfonyl, ($C_1$-$C_6$)alkoxy, —$(CH_2)_n$—$NR_3R_4$ and —NH—C(O)—CH($R_A$)—$NR_5R_6$;
$R_3$ and $R_4$ are, independently, selected from the group consisting of H, ($C_1$-$C_6$)alkyl and ($C_1$-$C_6$)alkyl-carbonyl;
$R_5$ and $R_6$ are, independently, H or ($C_1$-$C_6$)alkyl; or a pharmaceutically acceptable salt thereof.

14. A compound of claim 13 wherein
$Z'_2$ is phenyl substituted by at least two members selected from the group consisting of: fluoro, nitro, cyano, hydroxy, ($C_1$-$C_6$)alkyl-sulfonyl, ($C_1$-$C_6$)alkoxy, —$NH_2$ and —NH—C(O)—CH($R_A$)—$NR_5R_6$; $R_5$ and $R_6$ are, independently, H or ($C_1$-$C_6$)alkyl; or a pharmaceutically acceptable salt thereof.

15. A compound of claim 7, wherein
$Z'_2$ is selected from the group consisting of pyridinyl, pyrimidinyl, pyrazinyl, triazolyl, furyl, thienyl, purinyl, triazinyl, pyrrazolo-pyrimidinyl, quinoxalinyl and indolyl, each of these radicals being optionally substituted by at least one member selected from the group consisting of: halo, nitro, cyano, hydroxy, ($C_1$-$C_6$)alkyl and —$NH_2$; or a pharmaceutically acceptable salt thereof.

16. A compound of claim 1 selected from the group consisting of:
4-[4-(4-fluorophenoxy)phenyl]-2-(phenoxymethyl)-1H-imidazole;
4-(1,1'-biphenyl-4-yl)-2-[(phenylthio)methyl]-1H-imidazole;
4-(1,1'-biphenyl-4-yl)-2-(phenoxymethyl)-1H-imidazole;
4-[4-(4-fluorophenoxy)phenyl]-2-[(phenylthio)methyl]-1H-imidazole;
2-[(4-fluorophenoxy)methyl]-4-[4-(4-fluorophenoxy)phenyl]-1H-imidazole;
2-(phenoxymethyl)-4-[4-(phenylthio)phenyl]-1H-imidazole;
2-(phenoxymethyl)4-[4-phenylsulfonyl)phenyl]-1H-imidazole;
4-{4-[(2-fluorobenzyl)oxy]phenyl}-2-(phenoxymethyl)-1H-imidazole;
2-(phenoxymethyl)-4-(4-phenoxyphenyl)-1H -imidazole trifluoroacetate;
4-[4-(4-bromophenoxy)phenyl]-2-(phenoxymethyl)-1H-imidazole trifluoroacetate;
4-[4-(1H-imidazol-1-yl)phenyl]-2-(phenoxymethyl)-1H-imidazole;
4-[4-(4-methoxyphenoxy)phenyl]-2-(phenoxymethyl)-1H-imidazole;
4-(4-hexylphenyl)-2-(phenoxymethyl)-1H-imidazole;
4-(4-butoxyphenyl)-2-(phenoxymethyl)-1H-imidazole;
4-[4-(4-nitrophenoxy)phenyl]-2-(phenoxymethyl)-1H-imidazole;
4-(2-{4-[2-(phenoxymethyl)-1H-imidazol-4-yl]phenoxy}ethyl) morpholine;
1-(2-{4-[2-(phenoxymethyl)-1H-imidazol-4-yl]phenoxy}ethyl) piperidine hydrochloride;
N,N-dimethyl-N-(2-{4-[2-(phenoxymethyl)-1H-imidazol-4-yl]phenoxy}ethyl) amine hydrochloride;
4-[4-(2-methoxyethoxy)phenyl]-2-(phenoxymethyl)-1H-imidazole;
2-(phenoxymethyl)-4-[4-(4,4,4-trifluorobutoxy)phenyl]-1H-imidazole;
4-[4-(4-fluorophenoxy)phenyl]-5-methyl-2-(phenoxymethyl)-1H-imidazole;
4-fluoro-N-{4-[2-(phenoxymethyl)-1H-imidazol-4-yl]phenyl}benzamide;
4-{4-[2-(phenoxymethyl)-1H-imidazol-4-yl]phenoxy}benzonitrile;
ethyl 4-[2-(phenoxymethyl)-1H-imidazol-4-yl]benzoate;
ethyl 4-{4-[2-(phenoxymethyl)-1H-imidazol-4-yl]phenoxy}benzoate;
4-{4-[4-(methylthio)phenoxy]phenyl}-2-(phenoxymethyl)-1H-imidazole;
4-{4-[4-(methylsulfonyl)phenoxy]phenyl}-2-(phenoxymethyl)-1H-imidazole;
4-{4-[2-(phenoxymethyl)-1H-imidazol-4-yl]phenoxy}aniline hydrochloride;
{4-[2-(phenoxymethyl)-1H-imidazol-4-yl]phenyl}phenyl methanone trifluoroacetate;
N-(4-fluorophenyl)-4-[2-(phenoxymethyl)-1H-imidazol-4-yl]benzamide trifluoroacetate;
4-[4-(3-nitrophenoxy)phenyl]-2-(phenoxymethyl)-1H-imidazole;
3-{4-[2-(phenoxymethyl)-1H-imidazol-4-yl]phenoxy}aniline hydrochloride;
4-{4-[4-(benzyloxy)phenoxy]phenyl}-2-(phenoxymethyl)-1H-imidazole;
4-{4-[2-(phenoxymethyl)-1H-imidazol-4-yl]phenoxy}phenol;
4-[4-(3-fluorophenoxy)phenyl]-2-(phenoxymethyl)-1H-imidazole;
N-(4-{4-[2-(phenoxymethyl)-1H-imidazol-4-yl]phenoxy}phenyl) acetamide;
2-nitro-4-{4-[2-(phenoxymethyl)-1H-imidazol-4-yl]phenoxy}aniline trifluoroacetate;
N-methyl-N-(4-{4-[2-(phenoxymethyl)-1H-imidazol-4-yl]phenoxy}phenyl) amine;
3-{4-[2-(phenoxymethyl)-1H-imidazol-4-yl]phenoxy}benzonitrile;
4-[4-(2-nitrophenoxy)phenyl]-2-(phenoxymethyl)-1H-imidazole;
2-{4-[2-(phenoxymethyl)-1H-imidazol-4-yl]phenoxy}aniline hydrochloride;

1-(4-{4-[2-(phenoxymethyl)-1H-imidazol-4-yl]
 phenoxy}phenyl) methanamine hydrochloride;
1-(3-{4-[2-(phenoxymethyl)-1H-imidazol-4-yl]
 phenoxy}phenyl) methanamine hydrochloride;
4-[4-(3-bromophenoxy)phenyl]-2-(phenoxymethyl)-1H-
 imidazole;
2-fluoro-4-{4-[2-(phenoxymethyl)-1H-imidazol-4-yl]
 phenoxy}aniline hydrochloride;
4-[4-(3-chlorophenoxy)phenyl]-2-(phenoxymethyl)-1H-
 imidazole;
4-[4-(3,5-difluorophenoxy)phenyl]-2-(phenoxymethyl)-
 1H-imidazole;
4-(4-benzylphenyl)-2-(phenoxymethyl)-1H-imidazole;
4-[4-(3-methylphenoxy)phenyl]-2-(phenoxymethyl)-1H-
 imidazole;
4-[4-(2-chlorophenoxy)phenyl]-2-(phenoxymethyl)-1H-
 imidazole hydrochloride;
4-[4-(2-fluorophenoxy)phenyl]-2-(phenoxymethyl)-1H-
 imidazole;
4-[4-(3,4-difluorophenoxy)phenyl]-2-(phenoxymethyl)-
 1H-imidazole;
$N^1$-(4-{4-[2-(phenoxymethyl)-1H-imidazol-4-yl]
 phenoxy}phenyl) glycinamide hydrochloride;
4-[4-(2,5-difluorophenoxy)phenyl]-2-(phenoxymethyl)-
 1H-imidazole;
4-[4-(2,4-difluorophenoxy)phenyl]-2-(phenoxymethyl)-
 1H-imidazole;
4-[4-(2,3-difluorophenoxy)phenyl]-2-(phenoxymethyl)-
 1H-imidazole;
4-[4-(2,6-difluorophenoxy)phenyl]-2-(phenoxymethyl)-
 1H-imidazole.

17. A process for the preparation of a compound of claim 1 comprising reacting a compound of the formula

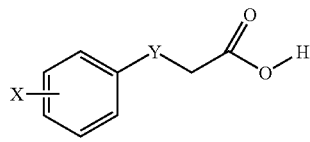
(II)

wherein X and Y have the meaning of claim 1 with a base to form a compound of formula (II) in a salified form, then with the α-halogeno-ketone of the formula

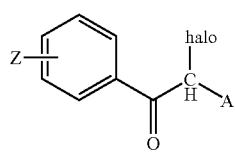
(II-ii)

in which Z and A have the meaning of claim 1, in an inert solvent, then the keto-ester thus obtained is cyclized in the presence of an ammonium salt to produce the compound of claim 1.

18. A process for the preparation of a compound of claim 1 comprising reacting a compound of the formula II-iii

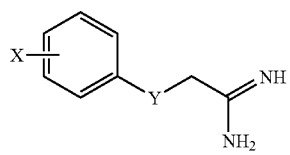

wherein X and Y have the meaning of claim 1, and an α-halogeno-ketone of the formula

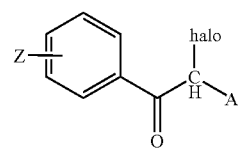
(II.ii)

in which Z and A are as defined in claim 1 by condensing under reflux in a polar inert solvent.

19. A pharmaceutical composition containing, as active ingredient, at least one compound of claim 1 with a pharmaceutically acceptable support.

20. A method of inhibiting tubulin polymerization in warm-blooded animals comprising administering to warm-blooded animals in need thereof of an amount of a compound of claim 1 sufficient to inhibit tubulin polymerization.

21. The method of claim 20 using a compound of the formula

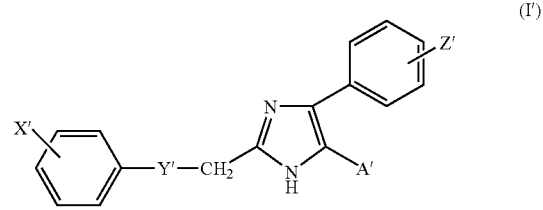
(I')

in racemic, enantiomeric form or any combinations of these forms, wherein
 X' is H and halo;
 Y is —O— or —S—;
 A' is H or $(C_1-C_6)$alkyl
 Z' is a member selected from the group consisting of:
  $(C_1-C_6)$alkyl optionally substituted by at least one halo;
  aryl optionally substituted by at least one halo, nitro, cyano, hydroxy, $(C_1-C_6)$alkyl optionally by at least one halo, —$(CH_2)_n$—$NR_3R_4$, $(C_1-C_6)$alkyl-sulfonyl, $(C_1-C_6)$alkyl-thio, $(C_1-C_6)$alkoxy optionally substituted by at least one halo, $(C_1-C_6)$alkoxy-carbonyl, phosphate, sulfate, glycoside and —NH—C(O)—CH$(R_A)$—$NR_5R_6$;
  aryl-$(C_1-C_6)$alkyl;
  heteroaryl;
  -$Z_1$-$Z'_1$;
  —$NR_N$—C(O)-$Z'_2$; and
  -$Z_2$-$Z'_2$;
 $Z_1$ is selected from the group consisting of —O—, —C(O)—O—, —$NR_N$—C(O)— and —C(O)—$NR_N$;
 $Z'_1$ is selected from the group consisting of $(C_1-C_{10})$alkyl; aryl-$(C_1-C_6)$alkyl, the aryl of which is optionally substituted by at least one halo; and $(C_1-C_6)$alkyl substituted by at least one member selected from the group consisting of halo, $(C_1-C_6)$alkoxy, $(C_1-C_6)$alkylthio and —$NR_1R_2$;
 $R_1$ and $R_2$ are, independently, H or $(C_1-C_6)$alkyl, or form together with the nitrogen atom to which they are attached, a heterocycloalkyl optionally substituted by $(C_1-C_6)$alkyl;
 $Z_2$ is selected from the group consisting from —O—, —S—, —$SO_2$—, —C(O)—, —C(O)—$NR_N$— and —$NR_N$—;

$Z'_2$ is aryl or heteroaryl, the aryl and heteroaryl being optionally substituted by at least one member selected from the group consisting of:
   halo, nitro, cyano, hydroxy, $(C_1\text{-}C_6)$alkyl optionally substituted by at least one halo, $(C_1\text{-}C_6)$alkyl-thio, $(C_1\text{-}C_6)$alkyl-sulfonyl, $(C_1\text{-}C_6)$alkoxy optionally substituted by at least one halo, aryl-alkoxy, $(C_1\text{-}C_6)$alkoxy-carbonyl, phosphate, sulfate, glycoside, —$(CH_2)_n$—$NR_3R_4$ and —NH—C(O)—CH($R_A$)—$NR_5R_6$;

$R_3$ and $R_4$ are, independently, selected from the group consisting of H or $(C_1\text{-}C_6)$alkyl, $(C_1\text{-}C_6)$alkyl-carbonyl and $(C_1\text{-}C_6)$alkyl-sulfonyl, or $R_3$ and $R_4$ form together with the nitrogen atom to which they are attached, a heteroaryl or a heterocycloalkyl optionally substituted by $(C_1\text{-}C_6)$alkyl;

$R_5$ and $R_6$ are, independently, H or $(C_1\text{-}C_6)$alkyl;

$R_A$ is the residue of an amino acid of the formula $NH_2$—CH($R_A$)—C(O)—OH;

$R_N$ is hydrogen or $(C_1\text{-}C_6)$alkyl;

n is an integer from 0 to 3; or a pharmaceutically acceptable salt thereof.

* * * * *